US011547756B2

(12) United States Patent
Kallewaard-Lelay et al.

(10) Patent No.: US 11,547,756 B2
(45) Date of Patent: Jan. 10, 2023

(54) METHOD OF TREATING INFLUENZA A

(71) Applicant: MEDIMMUNE, LLC, Gaithersburg, MD (US)

(72) Inventors: Nicole Kallewaard-Lelay, Gaithersburg, MD (US); Raburn Mallory, Gaithersburg, MD (US); Gabriel Robbie, Gaithersburg, MD (US); Song Ren, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 0 days.

(21) Appl. No.: 16/984,827

(22) Filed: Aug. 4, 2020

(65) Prior Publication Data
US 2020/0397899 A1 Dec. 24, 2020

Related U.S. Application Data

(63) Continuation of application No. 16/068,941, filed as application No. PCT/US2017/013086 on Jan. 12, 2017, now abandoned.

(60) Provisional application No. 62/278,068, filed on Jan. 13, 2016.

(51) Int. Cl.
*A61K 39/42* (2006.01)
*A61K 31/215* (2006.01)
*A61P 31/16* (2006.01)
*C07K 16/10* (2006.01)
*A61K 31/13* (2006.01)
*A61K 31/7012* (2006.01)
*A61K 39/00* (2006.01)

(52) U.S. Cl.
CPC .............. *A61K 39/42* (2013.01); *A61K 31/13* (2013.01); *A61K 31/215* (2013.01); *A61K 31/7012* (2013.01); *A61P 31/16* (2018.01); *C07K 16/1018* (2013.01); *A61K 2039/505* (2013.01); *A61K 2039/545* (2013.01); *C07K 2317/21* (2013.01); *C07K 2317/33* (2013.01); *C07K 2317/76* (2013.01); *C07K 2317/94* (2013.01); *C12N 2760/16111* (2013.01)

(58) Field of Classification Search
None
See application file for complete search history.

(56) References Cited

U.S. PATENT DOCUMENTS

| | | |
|---|---|---|
| 3,766,162 A | 10/1973 | Spector |
| 3,791,932 A | 2/1974 | Schuurs et al. |
| 3,817,837 A | 6/1974 | Rubenstein et al. |
| 4,179,337 A | 12/1979 | Davis et al. |
| 4,233,402 A | 11/1980 | Maggio et al. |
| 4,495,285 A | 1/1985 | Shimizu et al. |
| 4,609,546 A | 9/1986 | Hiratani |
| 4,676,980 A | 6/1987 | Segal et al. |
| 4,766,106 A | 8/1988 | Katre et al. |
| 4,831,175 A | 5/1989 | Gasnow et al. |
| 5,595,721 A | 1/1997 | Kaminski et al. |
| 5,807,715 A | 9/1998 | Morrison et al. |
| 6,300,064 B1 | 10/2001 | Knappik et al. |
| 6,300,104 B1 | 10/2001 | Morrison et al. |
| 8,101,553 B1 | 1/2012 | Kurosawa et al. |
| 8,871,207 B2 | 10/2014 | Lanzavecchia |
| 9,243,054 B2 | 1/2016 | Burioni et al. |
| 9,340,603 B2 | 5/2016 | Lanzavecchia |
| 10,442,854 B2 | 10/2019 | Kallewaard-Lelay et al. |
| 10,494,419 B2 | 12/2019 | Benjamin et al. |
| 10,519,221 B2 | 12/2019 | Kallewaard-Lelay et al. |
| 2007/0219149 A1 | 9/2007 | Hasegawa et al. |
| 2010/0080813 A1 | 4/2010 | Lanzavecchia |
| 2011/0014187 A1 | 1/2011 | Burioni et al. |
| 2012/0128684 A1 | 5/2012 | Marasco et al. |
| 2016/0257732 A1 | 9/2016 | Benjamin et al. |
| 2017/0218054 A1 | 8/2017 | Kallewaard-Lelay et al. |
| 2018/0155413 A1 | 6/2018 | Kallewaard-Lelay et al. |
| 2019/0015509 A1 | 1/2019 | Kallewaard-Lelay et al. |
| 2020/0109187 A1 | 4/2020 | Kallewaard-Lelay et al. |

FOREIGN PATENT DOCUMENTS

| | | |
|---|---|---|
| EP | 1167382 A1 | 1/2002 |
| EP | 2919813 B1 | 10/2018 |
| JP | A 2014-527403 A | 10/2014 |
| JP | A 2015-501815 A | 1/2015 |
| RU | 2536956 C1 | 12/2014 |
| WO | WO00/52031 A2 | 9/2000 |
| WO | WO00/52473 A2 | 9/2000 |
| WO | WO2004/001007 A1 | 12/2003 |
| WO | WO2004/007667 A2 | 1/2004 |
| WO | 2005/007697 A1 | 1/2005 |
| WO | WO2006/124269 A2 | 11/2006 |
| WO | WO2007/045477 A2 | 4/2007 |
| WO | WO2007/109742 A2 | 9/2007 |

(Continued)

OTHER PUBLICATIONS

Any references not provided herewith were previously cited and submitted in U.S. Appl. No. 16/068,941, filed Jul. 10, 2018 to which this application claims priority.
Abed et al., "A Review of Clinical Influenza A and B Infections with Reduced Susceptibility to Both Oseltamivir and Zanamivir," Open Forum Infectious Diseases 4(3): ofx105 (2017).
Ali et al., "Evaluation of MEDI8852, an Anti-Influenza A Monoclonal Antibody, in Treating Acute Uncomplicated Influenza," Antimicrobial Agents and Chemotherapy 62(11): e00694-18 (2018).
Benjamin et al., "A Broadly Neutralizing Human Monoclonal Antibody Directed against a Novel Conserved Epitope on the Influenza Virus H3 Hemagglutinin Globular Head," J Virol 88(12):6743-6750 (2014).

(Continued)

*Primary Examiner* — Benjamin P Blumel
(74) *Attorney, Agent, or Firm* — Medler, Ferro, Woodhouse & Mills PLLC

(57) ABSTRACT

Provided herein are methods for treating, reducing or preventing influenza A virus infection in a patient, as well as compositions and articles of manufacture for treating, reducing or preventing influenza A virus infection in a patient.

11 Claims, 2 Drawing Sheets

Specification includes a Sequence Listing.

(56) References Cited

FOREIGN PATENT DOCUMENTS

| | | |
|---|---|---|
| WO | WO2007/117577 A2 | 10/2007 |
| WO | WO2007/134327 A2 | 11/2007 |
| WO | WO2008/028946 A2 | 3/2008 |
| WO | WO2008/054606 A2 | 5/2008 |
| WO | WO2008/066691 A2 | 6/2008 |
| WO | WO2008/076379 A2 | 6/2008 |
| WO | WO2008/084410 A2 | 7/2008 |
| WO | WO2008/110937 A2 | 9/2008 |
| WO | WO2009/115972 A1 | 9/2009 |
| WO | WO2010/010466 A2 | 1/2010 |
| WO | WO2010/010467 A2 | 1/2010 |
| WO | WO2010/054007 A1 | 5/2010 |
| WO | WO2012/082634 A1 | 6/2012 |
| WO | WO2013/007770 A1 | 1/2013 |
| WO | WO2013/011347 A1 | 1/2013 |
| WO | WO2013/043729 A1 | 3/2013 |
| WO | WO2013/044203 A2 | 3/2013 |
| WO | WO2013/086052 A2 | 6/2013 |
| WO | WO2013/132007 A1 | 9/2013 |
| WO | WO2014/078268 A1 | 5/2014 |
| WO | WO2014/158001 A1 | 10/2014 |
| WO | WO2015/051010 A1 | 4/2015 |
| WO | WO2016/011035 A2 | 1/2016 |
| WO | WO2016/196470 A1 | 12/2016 |
| WO | WO2017/123685 A1 | 7/2017 |
| WO | WO2017/147248 A1 | 8/2017 |

OTHER PUBLICATIONS

Biere et al., "Differentiation of Influenza B Virus Lineages Yamagata and Victoria by Real-Time PCR," J Clin Microbiol 48:1425-1427 (2010).
Bouvier, "The Future of Influenza Vaccines: A Historical and Clinical Perspective," Vaccines 6:58 (2018).
Chai et al., "A broadly protective therapeutic antibody against influenza B virus with two mechanisms of action," Nature Comm 8:14234 (2017).
Corti et al., "Heterosubtypic neutralizing antibodies are produced by individuals immunized with a seasonal influenza vaccine," J Clin Invest 120:1663-1673 (2010).
Corti et al., "A Neutralizing Antibody Selected from Plasma Cells That Binds to Group 1 and Group 2 Influenza A Hemagglutinins," Science 333(6044):850-856 (2011).
Corti et al., "Cross-neutralization of four paramyxoviruses by a human monoclonal antibody," Nature 501(7467):439-443 (2013).
Corti et al., "Tackling influenza with broadly neutralizing antibodies," Curr Opin Virol 24:60-69 (2017).
Deyev and Lebedenko. "Modern Technologies for Creating Synthetic Antibodies for Clinical Application." Acta Naturae 1:32-50 (2009).
Dreyfus et al., "Highly Conserved Protective Epitopes on Influenza B Viruses," Science 337(6100):1343-1348 (2012).
Ekiert et al., "Antibody recognition of a highly conserved influenza virus epitope: implications for universal prevention and therapy," Science 324(5924):246-251 (2009).
Ekiert et al., "A Highly Conserved Neutralizing Epitope on Group 2 Influenza A Viruses," Science 333(6044):843-850 (2011).
Ekiert et al., "Cross-neutralization of influenza A viruses mediated by a single antibody loop," Nature 489(7417):526-532 (2012).
Friesen et al., "A common solution to group 2 influenza virus neutralization," Proc Natl Acad Sci USA 111(1):445-450 (2014).
Genbank Accession ID AAK94805.1, immunoglobulin light chain variable region, partial [Homo sapiens], published Dec. 31, 2001.
Genbank Accession ID ACS95408.1, immunoglobulin heavy chain variable region, partial [Homo sapiens], published Dec. 31, 2001.
Gerhard et al., "Prospects for Universal Influenza Virus Vaccine," Emerg Infect Dis 12(4):569-574 (2006).
Gioia et al., "Cross-subtype Immunity against Avian Infl uenza in Persons Recently Vaccinated for Influenza," Emerg Infect Dis 14(1):121-128 (2008).

Greenspan et al., "Defining epitopes: It's not as easy as it seems," Nature Biotechnol 17:936-937 (1999).
Hassantoufighi et al., "A practical influenza neutralization assay to simultaneously quantify hemagglutinin and neuraminidase-inhibiting antibody responses," Vaccine 28:790-797 (2010).
Ignatiev, Anna Viktorovna, "Features of the antigenic structure of hemagglutinin recognized by antibodies against modern influenza A viruses of subtypes H5 and H1." Virology (2012).
Kallewaard et al., "Structure and Function Analysis of an Antibody Recognizing All Influenza A Subtypes," Cell 166: 596-608 (2016).
Kashyap et al., "Combinatorial antibody libraries from survivors of the Turkish H5N1 avian influenza outbreak reveal virus neutralization strategies," Proc Natl Acad Sci USA 105(16):5986-5991 (2008).
Kaverin et al., "Epitope Mapping of the Hemagglutinin Molecule of a Highly Pathogenic H5N1 Influenza Virus by Using Monoclonal Antibodies," J Virol 81(23):12911-12917 (2007).
Kozbor et al., "The production of monoclonal antibodies from human lymphocytes," Immunol Today 4(3):72-79 (1983).
Krause et al., "A Broadly Neutralizing Human Monoclonal Antibody That Recognizes a Conserved, Novel Epitope on the Globular Head of the Influenza H1N1 Virus Hemagglutinin," J Virol 85(20):10905-10908 (2011).
Lee et al., "Heterosubtypic antibody recognition of the influenza virus hemagglutinin receptor binding site enhanced by avidity," Proc Natl Acad Sci USA 109(42):17040-17045 (2012).
Li et al., "Pandemic H1N1 influenza vaccine induces a recall response in humans that favors broadly cross-reactive memory B cells," Proc Natl Acad Sci USA 109(23):9047-9052 (2012).
Lin et al., "Recent changes among human influenza viruses." Virus Res. 103:47-52 (2004).
Nakamura et al., "An In Vivo Human-Plasmablast Enrichment Technique Allows Rapid Identification of Therapeutic Influenza A Antibodies," Cell Host Microbe 14:93-103 (2013).
Nguyen et al., "Heterosubtypic Immunity to Influenza A Virus Infection Requires B Cells but Not CD8+ Cytotoxic T Lymphocytes," J Virol 183:368-376 (2001).
Okuno et al., "A Common Neutralizing Epitope Conserved between the Hemagglutinins of Influenza A Virus H1 and H2 Strains," J Virol 67(5):2552-2558 (1993).
Pakula and Sauer, "Genetic Analysis of Protein Stability and Function," Annu. Rev. Genet. 23:289-310 (1989).
Pan et al., "Weight-based Dosing in Medication Use: What Should We Know?" Patient Preference and Adherence 10: 549-560 (2016).
Pappas et al., "Rapid development of broadly influenza neutralizing antibodies through redundant mutations," Nature 516(7531):418-422 (2014).
Paul et al., eds. Fundamental Immunology $3^{rd}$ Edition (1993), pp. 292-295.
Prabhu et al., "Monoclonal Antibodies against the Fusion Peptide of Hemagglutinin Protect Mice from Lethal Influenza A Virus H5N1 Infection," J Virol 83(6):2553-2562 (2009).
Ren et al., "Epitope-focused vaccine design against influenza A and B viruses," Curr Opin Immunol 42:83-90 (2016).
Roit, Ivan M. (1991) Essential Immunology ($7^{th}$ Ed.) Blackwell Science, Inc.
Rowe et al., "Detection of Antibody to Avian Influenza A (H5N1) Virus in Human Serum by Using a Combination of Serologic Assays," J Clin Microbiol 37(4):937-943 (1999).
Rudikoff et al., "Single amino acid substitution altering antigen-binding specificity," Proc Natl Acad Sci USA 79(6):1979-1983 (1982).
Simmons et al., "Prophylactic and Therapeutic Efficacy of Human Monoclonal Antibodies against H5N1 Influenza," PLOS Med 4(5):e178 (2007).
Smirnov et al., "Prevention and treatment of bronchopneumonia in mice caused by mouse-adapted variant of avian H5N2 influenza A virus using monoclonal antibody against conserved epitope in the HA stem region," Arch Virol 145:1733-1741 (2000).
Sui et al., "Structural and functional bases for broad-spectrum neutralization of avian and human influenza A viruses," Nature Struct Mol Biol 16(3):265-273 (2009).

(56) References Cited

OTHER PUBLICATIONS

Temperton et al., "Longitudinally Profiling Neutralizing Antibody Response to SARS Coronavirus with Pseudotypes," Emerg Infect Dis 11(3):411-416 (2005).
Thompson et al., "Influenza-Associated Hospitalizations in the United States," JAMA 292:1333-1340 (2004).
Throsby et al., "Heterosubtypic Neutralizing Monoclonal Antibodies Cross-Protective against H5N1 and H1N1 Recovered from Human IgM+ Memory B Cells," PLOS One 3(12):e3942 (2008).
Traggiai et al., "An efficient method to make human monoclonal antibodies from memory B cells: potent neutralization of SARS coronavirus," Nature Med 10:871-875 (2004).
Vareckova et al., "HA2-specific monoclonal antibodies as tools for differential recognition of influenza A virus antigenic subtypes," Virus Res 132(1-2):181-186 (2008).
Wagner et al., "Bispecific antibody generated with sortase and click chemistry has broad antiinfluenza activity," Proc Natl Acad Sci USA 111(47):16820-16825 (2014).
Wang, Qinghua et al., "Crystal Structure of Unliganded Influenza B Virus Hemagglutinin," J Virol 82(6):3011-3020 (2008).
Wang, Tala T. et al., "Broadly Protective Monoclonal Antibodies against H3 Influenza Viruses following Sequential Immunization with Different Hemagglutinins," PLOS Pathog 6(2):e1000796 (2010).
Whittle et al., "Broadly neutralizing human antibody that recognizes the receptor-binding pocket of influenza virus hemagglutinin," Proc Natl Acad Sci USA 108(34):14216-14221 (2011).
Wilson et al., "Structure of the hemagglutinin membrane glycoprotein of influenza virus at 3 Å resolution," Nature 289:366-373 (1981).
Wrammert et al., "Rapid Cloning of High Affinity Human Monoclonal Antibodies Against Influenza Virus," Nature 453(7195):667-671 (2008).
Wrammert et al., "Broadly cross-reactive antibodies dominate the human B cell response against 2009 pandemic H1N1 influenza virus infection," J Exp Med 208(1):181-193 (2011).
Xiang et al., "Framework Residues 71 and 93 of the Chimeric B72.3 Antibody are Major Determinants of the Conformation of Heavy-chain Hypervariable Loops," J Mol Biol 253:385-390 (1995).
Yasugi et al., "Human Monoclonal Antibodies Broadly Neutralizing against Influenza B Virus," PLOS Pathog 9(2):e1003150 (2013).
Yoshida et al., "Cross-Protective Potential of a Novel Monoclonal Antibody Directed against Antigenic Site B of the Hemagglutinin of Influenza A Viruses," PLOS Pathog 5(3):e1000350 (2009).
Zabetakis et al., "Contributions of the Complementarity Determining Regions to the Thermal Stability of a Single-Domain Antibody," PLoS One 8(10):e77678 (2013).
Zhou et al., "Hospitalizations Associated With Influenza and Respiratory Syncytial Virus in the United States, 1993-2008," Clin Infect Dis 54(10):1427-1436.
Non-final Office Action issued in U.S. Appl. No. 15/026,276, dated Apr. 6, 2018.
Non-final Office Action issued in U.S. Appl. No. 15/026,276, dated Oct. 19, 2018.
Non-final Office Action issued in U.S. Appl. No. 15/026,276, dated Apr. 17, 2019.
Non-final Office Action issued in U.S. Appl. No. 15/325,603, dated Jun. 27, 2017.
Final Office Action issued in U.S. Appl. No. 15/325,603, dated Mar. 8, 2018.
Non-final Office Action issued in U.S. Appl. No. 15/325,603, dated Sep. 7, 2018.
Non-final Office Action issued in U.S. Appl. No. 15/577,799, dated Feb. 21, 2019.
Non-final Office Action issued in U.S. Appl. No. 16/068,941, dated Oct. 21, 2019.
Office Action in U.S. Appl. No. 16/068,941 dated Feb. 5, 2020.
Office Action in U.S. Appl. No. 16/560,040 dated Apr. 16, 2020.
Office Action in Australian Application No. 2014329609 dated Mar. 8, 2019.
Office Action in Australian Application No. 2015289805 dated Feb. 19, 2020.
Office Action in Chinese Application No. 201580038244.1 dated Jan. 17, 2020.
Office Action in Chinese Application No. 2014800539693.3 dated May 7, 2019.
Office Action in Chinese Application No. 201480053969.3 dated Feb. 3, 2020.
European Search Report in Application No. 14850550.6 dated Jul. 28, 2017.
European Search Report in Application No. 15821645.7 dated Mar. 26, 2018.
Office Action in European Application No. 15821645.7 dated Jul. 9, 2020.
Extended European Search Report dated Sep. 19, 2019.
Office Action in Japanese Application No. 2016-546872 dated Aug. 28, 2018.
Office Action in Japanese Application No. 2017-561892 dated Jun. 2, 2020.
Office Action in Japanese Application No. 2017-523183 dated Aug. 20, 2019.
Office Action in Mexican Application No. MX/a/2016/004067 dated Jul. 3, 2019.
Office Action in Russian Application No. 2016117053 dated Jun. 9, 2016.
Office Action in Russian Application No. 2016117053 dated Aug. 14, 2018.
Search Report in Russian Application No. 2020100073 dated May 28, 2020.
Office Action in Russian Application No. 2020100073 dated Jun. 10, 2020.
Russian Office Action Search Report dated Jul. 1, 2019.
Russian Office Action dated Nov. 6, 2019.
Office Action in Taiwanese Application No. 103134457 dated Apr. 11, 2018.
Office Action in Taiwanese Application No. 107146861 dated Feb. 6, 2020.
International Search Report issued in PCT/US2014/058652 dated Jan. 29, 2015.
Preliminary Report on Patentability issued in PCT/US2014/058652 dated Apr. 5, 2016.
International Search Report issued in PCT/US2015/040385 dated Dec. 23, 2015.
Preliminary Report on Patentability issued in PCT/US2015/040385 dated Jan. 17, 2017.
International Search Report issued in PCT/US2016/035026 dated Aug. 18, 2016.
International Search Report and Written Opinion issued in corresponding PCT/US2017/013086, dated Mar. 31, 2017.
Centers for Disease Control and Prevention. "Influenza (Flu): Antiviral drugs for seasonal influenza: additional links and resources." Jan. 7, 2021.
Davies and Riechmann. "Affinity improvement of single antibody VH domains: residues in all three hypervariable regions affect antigen binding." Immunotechnology. 2:169-179 (1996).
Deyde et al. "Surveillance of resistance to adamantanes among influenza A(H3N2) and A(H1N1) viruses isolated worldwide." JID 196:249 (2007).
Duwe, S. "Influenza viruses—antiviral therapy and resistance." GMS Infect Dis 5:ISSN 2195-8831 (2017).
Fan et al. "Bispecific antibodies and their applications." J. Hematol. Oncol. 8:130 (2015).
Holliger et al. "'Diabodies': small bivalent and bispecific antibody fragments." 90:6444-6448 (1993).
Holt et al. "Domain antibodies: proteins for therapy." Trends Biotech. 21 (11):484 (2003).
Lamepjo, T. "Influenza and antiviral resistance: an overview." Eur. J. Clin. Microbiol. Infect. Dis. (2020) doi.org/10.1007/s10096-020-03840-9.

METHOD OF TREATING INFLUENZA A

CROSS REFERENCE TO RELATED APPLICATIONS

This application is a continuation of U.S. application Ser. No. 16/068,941, which is a U.S. National Stage Application of International Application No. PCT/US2017/013086, filed on Jan. 12, 2017, said International Application No. PCT/US2017/013086 claims benefit under 35 U.S.C. § 119(e) of the U.S. Provisional Application No. 62/278,068, filed Jan. 13, 2016. Each of the above listed applications is incorporated by reference herein in its entirety for all purposes.

REFERENCE TO SEQUENCE LISTING SUBMITTED ELECTRONICALLY

The content of the sequence listing filed with the application is incorporated herein by reference in its entirety. This application incorporates by reference a Sequence Listing submitted with this application as text filed FLUA200P1_seq_listing created on Jan. 12, 2015 and having a size of 5.21 kilobytes.

FIELD OF THE INVENTION

The invention relates to methods, compositions and articles of manufacture for treating, reducing or preventing influenza A virus infection in a subject.

BACKGROUND TO THE INVENTION

Influenza viruses cause annual influenza epidemics and occasional pandemics, which pose a significant threat to public health worldwide. Seasonal influenza infection is associated with 200,000-500,000 deaths each year, particularly in young children, immunocompromised patients and the elderly. Mortality rates typically increase further during seasons with pandemic influenza outbreaks. There remains a significant unmet medical need for potent anti-viral therapeutics for preventing and treating influenza infections, particularly in under-served populations.

There are three types of influenza viruses, types A, B and C. Influenza A viruses can infect a wide variety of birds and mammals, including humans, pigs, chickens and ferrets. Influenza A viruses can be classified into subtypes based on allelic variations in antigenic regions of two genes that encode surface glycoproteins hemagglutinin (HA) and neuraminidase (NA). HA is the receptor-binding and membrane fusion glycoprotein, which mediates viral attachment and entry into target cells; HA is the primary target of protective humoral immune responses. The HA protein is trimeric in structure and includes three copies of a single polypeptide precursor, HA0, which, upon proteolytic maturation, is cleaved into a pH-dependent, metastable intermediate containing the globular head (HA1) and the stalk region (HA2). The membrane distal "globular head" constitutes the majority of the HA1 structure and contains the sialic acid binding pocket for viral entry and major antigenic domains. The membrane proximal "stalk" structure, assembled from HA2 and some HA1 residues, contains the fusion machinery, which undergoes a conformational change in the low pH environment of late endosomes to trigger membrane fusion and penetration into cells. The degree of sequence homology between influenza A subtypes is less in the HA1 (34%-59% homology between subtypes) than in the HA2 region (51%-80% homology). Neutralizing antibodies elicited by influenza virus infection are often targeted to the variable HA1 globular head to prevent viral receptor binding and are frequently strain-specific. A few, broad cross-reactive monoclonal antibodies have been identified that target the globular head of HA (Krause et al., (2011) J. Virol. 85; Whittle et al., (2011) PNAS 108; Ekiert et al., (2012) Nature 489; Lee et al., (2012) PNAS 109). In contrast, the structure of the stalk region is relatively conserved and a handful of broadly neutralizing antibodies have recently been identified that bind to HA stalk to prevent the pH-triggered fusion step for viral entry (Ekiert et al., (2009) Science 324; Sui et al., (2009) Nat. Struct. Mol. Biol. 16; Wrammert et al., (2011) J. Exp. Med. 208; Ekiert et al., (2011) Science 333; Corti et al., (2010) J. Clin. Invest, 120; Throsby M., (2008) PLoS One 3). Most of these stalk reactive neutralizing antibodies are either specific to influenza A group 1 viruses or specific to group 2 viruses. Very recently, stalk binding antibodies were isolated that were cross-reactive to both groups 1 and 2 viruses (Corti et al., (2011) Science 333(6044):850-856; Li et al., (2012) PNAS 109: 9047-9052; and Dreyfus et al., (2012) Science 337 (6100):1343-1348; Nakamura et al., (2013) Cell Host & Microbe 14: 93-103).

Despite advances in vaccines and small-molecule antiviral therapeutics, there remains an unmet medical need for more effective treatment of influenza in populations at high risk for morbidity and mortality. In these patients, influenza infection can lead to severe complications and causes a significant burden to the overall healthcare system. Current standard of care for treatment of influenza has many limitations, including the potential for reduced effectiveness in older adults due to late presentation to care, the potential for resistance, and a limited therapeutic window.

MEDI8852 (represented, for example, by SEQ ID Nos: 1-10) is a potent broadly neutralizing IgG1 kappa monoclonal antibody, which binds a highly conserved hemagglutinin stalk region shared in viruses from all 18 influenza A virus subtypes and demonstrates coverage of both seasonal and pandemic influenza A subtypes. MEDI8852 potently neutralizes a large panel of viruses including seasonal H1N1 and H3N2 viruses, as well as influenza A subtypes that have the potential to cause pandemics such as H2, H4, H5, H6, H7, and H9. Additionally, it has been shown that infected cells can be cleared using MEDI8852 via Fc-effector function (i.e., antibody dependent cellular toxicity (ADCC), antibody-dependent cellular phagocytosis (ADCP), and complement-dependent cytotoxicity (CDC)), and MEDI8852 prevents influenza A virus infection by inhibiting viral fusion, HA protease cleavage (maturation), and cell-to-cell spread.

To date, pharmacological testing of MEDI8852 has been limited. Although pharmacologically relevant animal species models were used for pharmacokinetic and pharmacodynamics studies, the pharmacology of these models differs from the pharmacology of MEDI8852 in humans. Accordingly, there remains a need for methods for estimating a starting dose for MEDI8852 administration in humans, and a need for effective, but safe doses of MEDI8852 for the treatment of influenza A infection in humans.

SUMMARY

Provided herein are methods, compositions and articles of manufacture for treating, reducing or preventing influenza A virus infection in a patient.

In one embodiment, a method of treating, reducing or preventing influenza A virus infection in a patient is provided. In another embodiment, the method includes a step of administering to the patient at least about 200 mg and up to about 3,500 mg of anti-influenza A antibody or fragment thereof that is capable of binding to influenza A virus hemagglutinin of at least one group 1 subtype and at least one group 2 subtype of influenza A virus.

In one embodiment, the patient is human. In one embodiment, the anti-influenza A antibody or fragment thereof is administered parenterally. In a more particular embodiment, the anti-influenza A antibody or fragment thereof is administered intravenously. In one embodiment, the anti-influenza A antibody or fragment thereof is administered at a rate of at least about 1 mg/min and up to about 50 mg/min, at least about 5 mg/min and up to about 30 mg/min, or at least about 15 mg/min and up to about 25 mg/min.

In one embodiment, the anti-influenza A antibody or fragment thereof is administered after the patient is exposed to influenza A virus, infected with influenza A virus, exhibits symptoms of influenza A virus infection, or a combination thereof. In another embodiment, the anti-influenza A antibody or fragment thereof is administered before the patient is exposed to influenza A virus, infected with influenza A virus, or exhibits symptoms of influenza A virus infection. In one embodiment, the patient is sero-negative for influenza A virus. In another embodiment, the patient is sera-positive for influenza A virus. In another embodiment, the sera-status of the patient is unknown. In one embodiment, the anti-influenza A antibody or fragment thereof is administered to a subject within 30 days of exposure, infection, symptom onset, or a combination thereof.

In a more particular embodiment, anti-influenza A antibody or fragment thereof includes one or more heavy chain CDRs having an amino acid sequence at least 75% identical to an amino acid sequence selected from an amino acid sequence shown in SEQ ID NO:3, SEQ ID NO:4, and SEQ ID NO:5. In another embodiment, anti-influenza A antibody or fragment thereof includes one or more light chain CDRs having amino acid sequence at least 75% identical to an amino acid sequence selected from an amino acid sequence shown in SEQ ID NO:8, SEQ ID NO:9 and SEQ ID NO:10. In one embodiment, anti-influenza A antibody or fragment thereof includes one or more heavy chain CDRs having an amino acid sequence at least 75% identical to an amino acid sequence selected from SEQ ID NO:3, SEQ ID NO:4, and SEQ ID NO:5 and one or more light chain CDRs having amino acid sequence at least 75% identical to an amino acid sequence selected from an amino acid sequence shown in SEQ ID NO:8, SEQ ID NO:9 and SEQ ID NO:10. In one embodiment, anti-influenza A antibody or fragment thereof includes one or more heavy chain CDRs with an amino acid sequence selected from SEQ ID NO:3, SEQ ID NO:4, and SEQ ID NO:5. In one embodiment, anti-influenza A antibody or fragment thereof includes one or more light chain CDRs with an amino acid sequence selected from SEQ ID NO:8, SEQ ID NO:9 and SEQ ID NO:10. In another embodiment, anti-influenza A antibody or fragment thereof includes one or more heavy chain CDRs with an amino acid sequence selected from SEQ ID NO:3, SEQ ID NO:4, and SEQ ID NO:5 and one or more light chain CDRs with an amino acid sequence selected from SEQ ID NO:8, SEQ ID NO:9 and SEQ ID NO:10.

In one embodiment, anti-influenza A antibody or fragment thereof includes a VH having an amino acid sequence with at least 75% identity to the amino acid sequence of SEQ ID NO: 2. In one embodiment, anti-influenza A antibody or fragment thereof includes a VL having an amino acid sequence with at least 75% identity to the amino acid sequence of SEQ ID NO: 7. In one embodiment, anti-influenza A antibody or fragment thereof includes a VH having an amino acid sequence with at least 75% identity to the amino acid sequence of SEQ ID NO: 2 and a VL having an amino acid sequence with at least 75% identity to the amino acid sequence of SEQ ID NO: 7. In one embodiment, anti-influenza A antibody or fragment thereof includes a VH having an amino acid sequence shown in SEQ ID NO: 2. In one embodiment, anti-influenza A antibody or fragment thereof includes a VL having an amino acid sequence shown in SEQ ID NO: 7. In one embodiment, anti-influenza A antibody or fragment thereof includes a VH having an amino acid sequence shown in SEQ ID NO: 2 and a VL having an amino acid sequence shown in SEQ ID NO: 7.

In a more particular embodiment, the anti-influenza A antibody includes MEDI8852.

In another embodiment, a composition for treating, reducing or preventing influenza A virus infection in a patient is provided. In one embodiment, the composition includes anti-influenza A antibody or fragment thereof that is capable of binding to influenza A virus hemagglutinin of at least one group 1 subtype and at least one group 2 subtype of influenza A virus, wherein the composition is formulated for administering at least about 200 mg and up to about 3,500 mg of anti-influenza A antibody or fragment thereof. In one embodiment, the composition includes anti-influenza A antibody or fragment thereof that is capable of binding to influenza A virus hemagglutinin and neutralizing at least one group 1 subtype and at least one group 2 subtype of influenza A virus, wherein the composition is formulated for administering at least about 200 mg and up to about 3,500 mg of anti-influenza A antibody or fragment thereof to a patient. In one embodiment, the composition includes anti-influenza A antibody or fragment thereof that is capable of neutralizing one or more influenza A virus group 1 subtype selected from: H1, H2, H5, H6, H8, H9, H11, H12, H13, H16, H17, H18, and variants thereof; and one or more influenza A virus group 2 subtypes selected from: H3, H4, H7, H10, H14 and H15 and variants thereof.

In one embodiment, the composition includes anti-influenza A antibody or fragment thereof that is capable of binding to influenza A virus hemagglutinin of at least one group 1 subtype and at least one group 2 subtype of influenza A virus, wherein the composition is formulated for intravenous infusion in the amount of at least about 200 mg and up to about 3,500 mg. In one embodiment, the composition includes anti-influenza A antibody or fragment thereof that is capable of binding to and neutralizing at least one group 1 subtype and at least one group 2 subtype of influenza A virus, wherein the composition is formulated for intravenous infusion in the amount of at least about 200 mg and up to about 3,500 mg. In one embodiment, the composition includes anti-influenza A antibody or fragment thereof that is capable of neutralizing one or more influenza A virus group 1 subtype selected from: H1, H2, H5, H6, H8, H9, H11, H12, H13, H16, H17, H18, and variants thereof; and one or more influenza A virus group 2 subtypes selected from: H3, H4, H7, H10, H14 and H15 and variants thereof.

In one embodiment, the composition includes anti-influenza A antibody or fragment thereof that is capable of clearing one or more influenza A virus group 1 subtype selected from: H1, H2, H5, H6, H8, H9, H11, H12, H13, H16, H17, H18, and variants thereof; and one or more influenza A virus group 2 subtypes selected from: H3, H4, H7, H10, H14, H15 and variants thereof. In one embodiment, the anti-influenza A antibody or fragment thereof is capable of clearing one or more influenza A virus group 1 subtypes via a mechanism that includes ADCC, CDC, or a combination thereof.

In a more particular embodiment, the composition includes anti-influenza A antibody or fragment thereof with one or more heavy chain CDRs having an amino acid sequence at least 75% identical to an amino acid sequence selected from an amino acid sequence shown in SEQ ID NO:3, SEQ ID NO:4, and SEQ ID NO:5. In another embodiment, the composition includes anti-influenza A antibody or fragment thereof with one or more light chain CDRs having amino acid sequence at least 75% identical to an amino acid sequence selected from an amino acid sequence shown in SEQ ID NO:8, SEQ ID NO:9 and SEQ ID NO:10. In one embodiment, the composition includes anti-influenza A antibody or fragment thereof with one or more heavy chain CDRs having an amino acid sequence at least 75% identical to an amino acid sequence selected from SEQ ID NO:3, SEQ ID NO:4, and SEQ ID NO:5 and one or more light chain CDRs having amino acid sequence at least 75% identical to an amino acid sequence selected from an amino acid sequence shown in SEQ ID NO:8, SEQ ID NO:9 and SEQ ID NO:10. In one embodiment, the composition includes anti-influenza A antibody or fragment thereof with one or more heavy chain CDRs with an amino acid sequence selected from SEQ ID NO:3, SEQ ID NO:4, and SEQ ID NO:5. In one embodiment, the composition includes anti-influenza A antibody or fragment thereof with one or more light chain CDRs with an amino acid sequence selected from SEQ ID NO:8, SEQ ID NO:9 and SEQ ID NO:10. In another embodiment, the composition includes anti-influenza A antibody or fragment thereof with one or more heavy chain CDRs with an amino acid sequence selected from SEQ ID NO:3, SEQ ID NO:4, and SEQ ID NO:5 and one or more light chain CDRs with an amino acid sequence selected from SEQ ID NO:8, SEQ ID NO:9 and SEQ ID NO:10.

In one embodiment, the composition includes anti-influenza A antibody or fragment thereof with a VH having an amino acid sequence with at least 75% identity to the amino acid sequence of SEQ ID NO: 2. In one embodiment, the composition includes anti-influenza A antibody or fragment thereof with a VL having an amino acid sequence with at least 75% identity to the amino acid sequence of SEQ ID NO: 7. In one embodiment, the composition includes anti-influenza A antibody or fragment thereof with a VH having an amino acid sequence with at least 75% identity to the amino acid sequence of SEQ ID NO: 2 and a VL having an amino acid sequence with at least 75% identity to the amino acid sequence of SEQ ID NO: 7. In one embodiment, the composition includes anti-influenza A antibody or fragment thereof with a VH having an amino acid sequence shown in SEQ ID NO: 2. In one embodiment, the composition includes anti-influenza A antibody or fragment thereof with a VL having an amino acid sequence shown in SEQ ID NO: 7. In one embodiment, the composition includes anti-influenza A antibody or fragment thereof with a VH having an amino acid sequence shown in SEQ ID NO: 2 and a VL having an amino acid sequence shown in SEQ ID NO: 7. In one embodiment, the composition includes MEDI8852. In another embodiment, the composition includes MEDI8852 and a pharmaceutically acceptable carrier.

In another embodiment, an article of manufacture is provided that includes a container and a composition within the container, wherein the composition includes anti-influenza A antibody or fragment thereof that is capable of binding to influenza A virus hemagglutinin at least one group 1 subtype and at least one group 2 subtype of influenza A virus, and a label or package insert with instructions to administer at least about 200 mg and up to about 3,500 mg of an anti-influenza A antibody or fragment thereof to a patient. In another embodiment, an article of manufacture is provided that includes a container and a composition within the container, wherein the composition includes anti-influenza A antibody or fragment thereof that is capable of binding to influenza A virus hemagglutinin and neutralizing at least one group 1 subtype and at least one group 2 subtype of influenza A virus, and a label or package insert with instructions to administer at least about 200 mg and up to about 3,500 mg of an anti-influenza A antibody or fragment thereof to a patient.

In one embodiment, the article of manufacture includes a composition that includes anti-influenza A antibody or fragment thereof that is capable of neutralizing one or more influenza A virus group 1 subtype selected from: H1, H2, H5, H6, H8, H9, H11, H12, H13, H16, H17, H18, and variants thereof; and one or more influenza A virus group 2 subtypes selected from: H3, H4, H7, H10, H14, H15 and variants thereof.

In a more particular embodiment, the article of manufacture includes a composition that includes anti-influenza A antibody or fragment thereof with one or more heavy chain CDRs having an amino acid sequence at least 75% identical to an amino acid sequence selected from an amino acid sequence shown in SEQ ID NO:3, SEQ ID NO:4, and SEQ ID NO:5. In another embodiment, the article of manufacture includes a composition that includes anti-influenza A antibody or fragment thereof with one or more light chain CDRs having amino acid sequence at least 75% identical to an amino acid sequence selected from an amino acid sequence shown in SEQ ID NO:8, SEQ ID NO:9 and SEQ ID NO:10. In one embodiment, the article of manufacture includes a composition that includes anti-influenza A antibody or fragment thereof with one or more heavy chain CDRs having an amino acid sequence at least 75% identical to an amino acid sequence selected from SEQ ID NO:3, SEQ ID NO:4, and SEQ ID NO:5 and one or more light chain CDRs having amino acid sequence at least 75% identical to an amino acid sequence selected from an amino acid sequence shown in SEQ ID NO:8, SEQ ID NO:9 and SEQ ID NO:10. In one embodiment, the article of manufacture includes a composition that includes anti-influenza A antibody or fragment thereof with one or more heavy chain CDRs with an amino acid sequence selected from SEQ ID NO:3, SEQ ID NO:4, and SEQ ID NO:5. In one embodiment, the article of manufacture includes a composition that includes anti-influenza A antibody or fragment thereof with one or more light chain CDRs with an amino acid sequence selected from SEQ ID NO:8, SEQ ID NO:9 and SEQ ID NO:10. In another embodiment, the article of manufacture includes a composition that includes anti-influenza A antibody or fragment thereof with one or more heavy chain CDRs with an amino acid sequence selected from SEQ ID NO:3, SEQ ID NO:4, and SEQ ID NO:5 and one or more light chain CDRs with an amino acid sequence selected from SEQ ID NO:8, SEQ ID NO:9 and SEQ ID NO:10.

In one embodiment, the article of manufacture includes a composition that includes anti-influenza A antibody or fragment thereof with a VH having an amino acid sequence with at least 75% identity to the amino acid sequence of SEQ ID NO: 2. In one embodiment, the article of manufacture includes a composition that includes anti-influenza A antibody or fragment thereof with a VL having an amino acid sequence with at least 75% identity to the amino acid sequence of SEQ ID NO: 7. In one embodiment, the article of manufacture includes a composition that includes anti-influenza A antibody or fragment thereof with a VH having an amino acid sequence with at least 75% identity to the amino acid sequence of SEQ ID NO: 2 and a VL having an amino acid sequence with at least 75% identity to the amino acid sequence of SEQ ID NO: 7. In one embodiment, the article of manufacture includes a composition that includes anti-influenza A antibody or fragment thereof with a VH having an amino acid sequence shown in SEQ ID NO: 2. In one embodiment, the article of manufacture includes a composition that includes anti-influenza A antibody or fragment thereof with a VL having an amino acid sequence shown in SEQ ID NO: 7. In one embodiment, the article of manufacture includes a composition that includes anti-influenza A antibody or fragment thereof with a VH having an amino acid sequence shown in SEQ ID NO: 2 and a VL having an amino acid sequence shown in SEQ ID NO: 7.

In one embodiment, the article of manufacture includes a composition that includes MEDI8852. In another embodiment, the article of manufacture includes a composition that includes MEDI8852 and a pharmaceutically acceptable carrier.

DETAILED DESCRIPTION

Introduction

Figure 1:
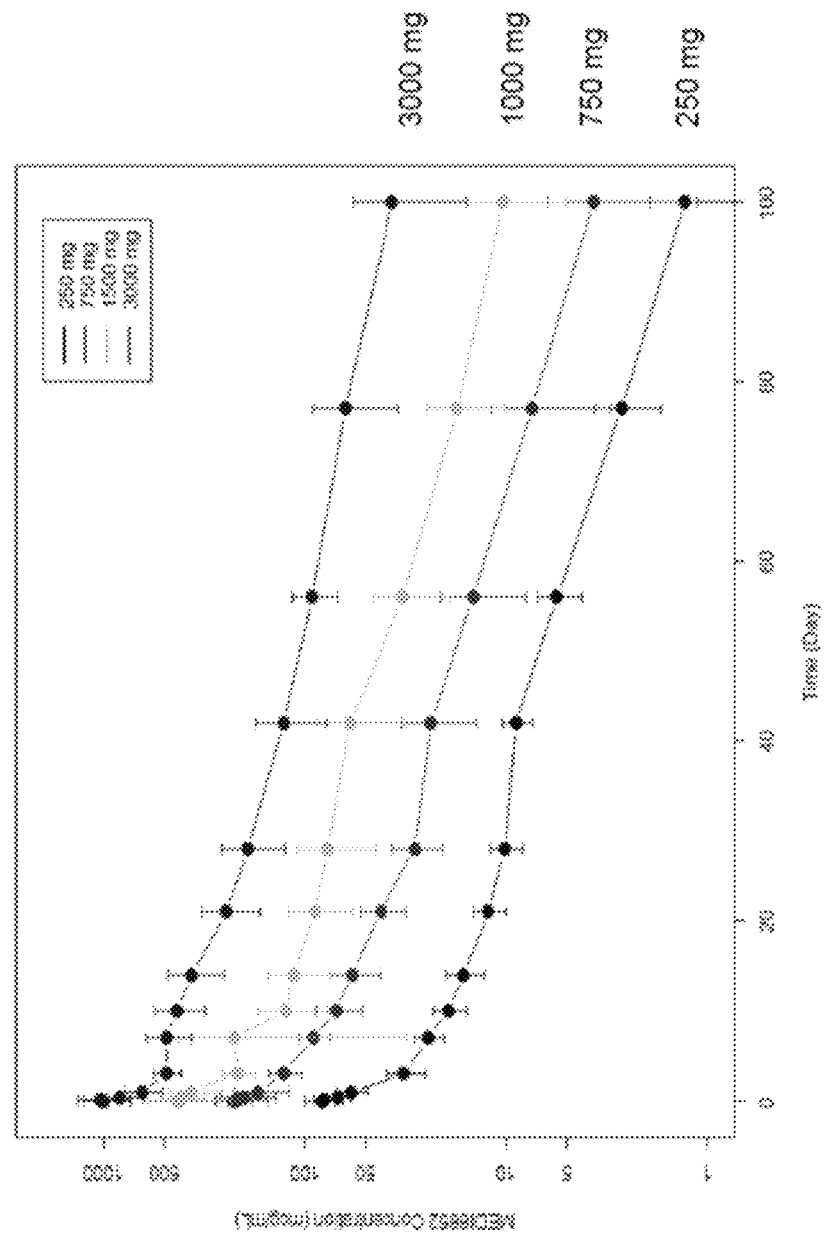
FIG. 1 is a graph showing mean (+/−standard deviation) concentration profiles for subjects treated with MEDI8852 at 250 mg, 750 mg, 1,500 mg and 3,000 mg, IV. (n=5-10/group/time point).

Described herein are methods, compositions, kits and articles of manufacture relating to the treatment, reduction, and/or prevention of influenza A virus infection in a subject.

Terminology

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise.

The term "about" refers to variation in the numerical quantity that can occur, for example, through typical measuring and handling procedures used for making compounds, compositions, concentrates or formulations; through inadvertent error in these procedures; through differences in the manufacture, source, or purity of starting materials or ingredients used to carry out the methods, and similar considerations. The term "about" also encompasses amounts that differ due to aging of compounds, compositions, concentrates or formulations with a particular initial concentration or mixture, and amounts that differ due to mixing or processing compounds, compositions, concentrates or formulations with a particular initial concentration or mixture. Where modified by the term "about" the claims appended hereto include equivalents to these quantities.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show (2002) 2nd ed. CRC Press; The Dictionary of Cell and Molecular Biology, 3rd ed. (1999) Academic Press; and the Oxford Dictionary Of Biochemistry And Molecular Biology, Revised (2000) Oxford University Press, provide one of skill with a general dictionary of many of the terms used in this invention.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The numbering of amino acids in the variable domain, complementarity determining region (CDRs) and framework regions (FR), of an antibody follow, unless otherwise indicated, the Kabat definition as set forth in Kabat et al., (1991) Sequences of Proteins of Immunological Interest, 5th Ed. Public Health Service, National Institutes of Health, Bethesda, Md. Using this numbering system, the actual linear amino acid sequence may contain fewer or additional amino acids corresponding to a shortening of, or insertion into, a FR or CDR of the variable domain. For example, a heavy chain variable domain may include a single amino acid insertion (residue 52a according to Kabat) after residue 52 of H2 and inserted residues (e.g. residues 82a, 82b, and 82c, etc., according to Kabat) after heavy chain FR residue 82. The Kabat numbering of residues may be determined for a given antibody by alignment at regions of homology of the sequence of the antibody with a "standard" Kabat numbered sequence. Maximal alignment of framework residues frequently requires the insertion of "spacer" residues in the numbering system, to be used for the Fv region. In addition, the identity of certain individual residues at any given Kabat site number may vary from antibody chain to antibody chain due to interspecies or allelic divergence.

Definitions

The term "nucleic acid" or "polynucleotide" encompasses any physical string of monomer units that correspond to a string of nucleotides, including, but not limited to, a polymer of nucleotides, including DNA and RNA polymers, and modified oligonucleotides, for example, oligonucleotides having bases that are not typical to biological RNA or DNA in solution, such as 2'-O-methylated oligonucleotides. A polynucleotide can include conventional phosphodiester bonds or non-conventional bonds, for example, an amide bond, such as found in peptide nucleic acids (PNA). A nucleic acid can be single-stranded or double-stranded. Unless otherwise indicated, a nucleic acid sequence encompasses complementary sequences, in addition to the sequence explicitly indicated.

The term "gene" is used broadly to refer to a nucleic acid associated with a biological function. Thus, genes include coding sequences and/or regulatory sequences required for their expression. The term "gene" applies to a specific genomic sequence, as well as to a cDNA or an mRNA encoded by that genomic sequence. Genes also include non-expressed nucleic acid sequences that, for example, form recognition sequences for other proteins. Non-expressed regulatory sequences include "promoters" and "enhancers," to which regulatory proteins such as transcription factors bind, resulting in transcription of adjacent or nearby sequences. For example, a polynucleotide which encodes a polypeptide can include a promoter and/or other transcription or translation control elements operably associated with one or more coding regions. "Operably associated" refers to a coding region for a gene product that is associated with one or more regulatory sequences in such a way as to place expression of the gene product under the influence or control of the regulatory sequence(s). "Expression of a gene" or "expression of a nucleic acid" refers to transcription of DNA into RNA, translation of RNA into a polypeptide, or both transcription and translation, as indicated by the context.

As used herein, the term "coding region" refers to a portion of nucleic acid which includes codons that can be translated amino acids. Although a "stop codon" (TAG, TGA, or TAA) is not translated into an amino acid, it is generally considered to be part of a coding region. However, flanking sequences, for example promoters, ribosome binding sites, transcriptional terminators, and introns, are not considered part of a coding region. A vector can contain a single coding region, or can include two or more coding regions. Additionally, a vector, polynucleotide, or nucleic acid can encode heterologous coding regions, either fused or unfused to a nucleic acid encoding a gene product of interest, for example, an antibody, or antigen-binding fragment, variant, or derivative thereof. Heterologous coding regions include, but are not limited to, specialized elements or motifs, such as a secretory signal peptide or a heterologous functional domain.

The term "vector" refers to the means by which a nucleic acid can be propagated and/or transferred between organisms, cells, or cellular components. Vectors include, but are not limited to, plasmids, viruses, bacteriophage, pro-viruses, phagemids, transposons, and artificial chromosomes, which are capable of replicating autonomously or integrating into a chromosome of a host cell. Vectors also include, but are not limited to: a naked RNA polynucleotide, a naked DNA polynucleotide, a polynucleotide that includes both DNA and RNA within the same strand, a poly-lysine-conjugated DNA or RNA, a peptide-conjugated DNA or RNA, a liposome-conjugated DNA, which are not autonomously replicating. An "expression vector" is a vector, such as a plasmid, which is capable of promoting expression as well as replication of a nucleic acid incorporated therein. Typically, the nucleic acid to be expressed is "operably linked" to a promoter and/or enhancer, and is subject to transcription regulatory control by the promoter and/or enhancer.

The term "host cell" refers to a cell which contains a heterologous nucleic acid, such as a vector, and supports the replication and/or expression of the nucleic acid. Host cells can be prokaryotic cells such as E. coli, or eukaryotic cells such as yeast, insect, amphibian, avian or mammalian cells, including human cells, for example, HEp-2 cells and Vero cells.

The term "introduced," when referring to a heterologous or isolated nucleic acid, refers to the transfer of a nucleic acid into a eukaryotic or prokaryotic cell where the nucleic acid can be incorporated into the genome of the cell, converted into an autonomous replicon, or transiently expressed. The term includes such methods as "infection," "transfection," "transformation" and "transduction." A variety of methods can be employed to introduce nucleic acids into host cells, including, but not limited to, electroporation, calcium phosphate precipitation, lipid mediated transfection, and lipofection.

The term "expression" refers to the process by which information from a gene is used in the synthesis of a functional gene product. Gene products are often proteins, but can also be functional RNA. Gene expression can be detected by determining the presence of corresponding rRNA, tRNA, mRNA, snRNA and/or gene products at the protein level.

The term "polypeptide" refers to a molecule that includes two or more amino acid residues linearly linked by amide bonds (also known as peptide bonds), such as a peptide or a protein. The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, and is not necessarily translated from a designated nucleic acid sequence. It can be generated in any manner, including by chemical synthesis. The amino acid residues of the polypeptide can be natural or non-natural and can be unsubstituted, unmodified, substituted or modified. An "amino acid sequence" is a polymer of amino acid residues, for example, a protein or polypeptide, or a character string representing an amino acid polymer, depending on context.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, with two pairs of polypeptide chains, each pair having one "light" and one "heavy" chain, wherein the variable regions of each light/heavy chain pair form an antibody binding site. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Typically, each heavy chain has at one end a variable domain (VH) followed by a number of constant domains (CH) and each light chain has a variable domain at one end (VL) and a constant domain (CL) at its other end wherein the constant domain of the light chain is aligned with the first constant domain of the heavy chain, and the light chain variable domain is aligned with the variable domain of the heavy chain.

The terms "antibody," "antibodies" and "immunoglobulins" as used herein encompass monoclonal antibodies (including full-length monoclonal antibodies), polyclonal antibodies, multispecific antibodies formed from at least two different epitope binding fragments (e.g., bispecific antibodies), CDR-grafted, human antibodies, humanized antibodies, camelised antibodies, chimeric antibodies, single-chain Fvs (scFv), single-chain antibodies, single domain antibodies, Fab fragments, Fab' fragments, F(ab')$_2$ fragments, antibody fragments that exhibit a desired biological activity (e.g., the antigen binding portion), disulfide-linked Fvs (dsFv), and anti-idiotypic (anti-Id) antibodies, intrabodies, and epitope-binding fragments or derivatives of any of the above. In particular, antibodies include immunoglobulin molecules and immunologically active fragments of immunoglobulin molecules that contain at least one antigen-binding site. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1 m(f, z, a or x), G2m(n), G3m(g, b, or c), Am, Em, and Km(1, 2 or 3)). Antibodies may be derived from any mammalian species, including, but not limited to, humans, monkeys, pigs, horses, rabbits, dogs, cats, and mice, or other animals such as birds, including, but not limited to, chickens. Antibodies may be fused to a heterologous polypeptide sequence, for example, a tag to facilitate purification.

The antibodies can be modified in the Fc region to provide desired effector functions or serum half-life. As discussed in more detail in the sections below, with the appropriate Fc regions, the naked antibody bound on the cell surface can induce cytotoxicity via antibody-dependent cellular cytotoxicity (ADCC), by recruiting complement in complement dependent cytotoxicity (CDC), or by recruiting nonspecific cytotoxic cells that express one or more effector ligands that recognize bound antibody on the Influenza A virus and subsequently cause phagocytosis of the cell in antibody dependent cell-mediated phagocytosis (ADCP), or some other mechanism. Alternatively, where it is desirable to eliminate or reduce effector function, for example, to reduce side effects or therapeutic complications, modified Fc regions may be used, for example to increase the binding affinity for FcRn and increase serum half-life. Alternatively, the Fc region can be conjugated to a moiety such as PEG or albumin to increase the serum half-life.

As used herein, the term "variant" refers to an antibody, which differs in amino acid sequence from a "parent" antibody amino acid sequence by virtue of addition, deletion and/or substitution of one or more amino acid residue(s) in the parent antibody sequence. A variant antibody may include one or more substitutions, deletions, including internal deletions, additions, including additions yielding fusion proteins, or conservative substitutions of amino acid residues of a parent antibody, including, for example MEDI8852 or in an amino acid sequence shown in SEQ ID NO: 2 or SEQ ID NO:7.

As used herein, the term "percent (%) sequence identity", or "homology" refers to the percentage of amino acid residues or nucleotides in a candidate sequence that are identical to the amino acid residues or nucleotides in a reference sequence, for example, a parent antibody sequence, after aligning the sequences and introducing gaps, if necessary, to achieve the maximum percent sequence identity, and not considering any conservative substitutions as part of the sequence identity. Alignment of the sequences may be produced manually or using the homology algorithm of Smith and Waterman (1981) Ads App. Math. 2, 482; the algorithm of Neddleman and Wunsch (1970) J. Mol. Biol. 48, 443; the method of Pearson and Lipman (1988) Proc. Natl Acad. Sci. USA 85, 2444, or using one or more computer programs based on these algorithms (GAP, BEST-FIT, FASTA, BLAST P, BLAST N and TFASTA in Wisconsin Genetics Software Package, Genetics Computer Group, 575 Science Drive, Madison, Wis.).

The term "conservative amino acid substitution" refers to the replacement of a first amino acid by a second amino acid that has chemical and/or physical properties (e.g, charge, structure, polarity, hydrophobicity/hydrophilicity) that are similar to those of the first amino acid. Conservative amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In addition, glycine and proline are residues that can influence chain orientation. Non-conservative substitutions will entail exchanging a member of one of these classes for a member of another class. Furthermore, if desired, non-classical amino acids or chemical amino acid analogs can be introduced as a substitution or addition into the antibody sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

Antibody variants can be generated by one or more amino acid alterations, including, for example, one or more substitutions, deletion and/or additions, introduced in one or more of the variable and/or framework regions of the antibody. One or more alterations of framework region residues may result in an improvement in the binding affinity of the antibody for the antigen. This may be especially true when these changes are made to humanized antibodies wherein the framework region may be from a different species than the CDR regions. Examples of framework region residues that might be modified include those which non-covalently bind antigen directly (Amit et al., (1986) Science, 233:747-753); interact with/effect the conformation of a CDR (Chothia et al., (1987) J. Mol. Biol., 196:901-917); and/or participate in the VL-VH interface (U.S. Pat. Nos. 5,225,539 and 6,548,640). In one embodiment, from about one to about five framework residues may be altered.

One useful procedure for generating altered antibodies is called "alanine scanning mutagenesis" (Cunningham and Wells, (1989) Science, 244:1081-1085). In this method, one or more of the hypervariable region residue(s) are replaced by alanine or polyalanine residue(s) to alter the interaction of the amino acids with the target antigen. Those hypervariable region residue(s) demonstrating functional sensitivity to the substitutions then are refined by introducing additional or other mutations at or for the sites of substitution. Thus, while the site for introducing an amino acid sequence variation is predetermined, the nature of the mutation per se need not be predetermined. The Ala-mutants produced this way can then be screened for biological activity.

The term "specifically binds," refers to the binding of an antibody or antigen binding fragment, variant, or derivative thereof to an epitope via its antigen binding domain more readily than it would bind to a random, unrelated epitope. The term "specificity" is used herein to qualify the relative affinity by which a certain antibody or fragment thereof binds to a certain epitope.

The term "epitope" as used herein refers to a protein determinant capable of binding to an antibody binding domain. Epitopes usually include chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. The term "discontinuous epitope" as used herein, refers to a conformational epitope on a protein antigen which is formed from at least two separate regions in the primary sequence of the protein.

As used herein, the term "affinity" refers to a measure of the strength of the binding of an individual epitope with the binding domain of an immunoglobulin molecule.

The term "isolated" refers to a biological material, such as a nucleic acid or a protein, which is substantially free from components that normally accompany or interact with it in its naturally occurring environment. Alternately, the isolated material may include material not found with the material in its natural environment. For example, if the material is in its natural environment, such as a cell, the material may have been placed at a location in the cell not native to material found in that environment. For example, a naturally occurring nucleic acid can be considered isolated if it is introduced by non-naturally occurring means to a locus of the genome not native to that nucleic acid. Such nucleic acids are also referred to as "heterologous" nucleic acids.

The term "recombinant" refers to a material that has been artificially or synthetically altered by human intervention. The alteration can be performed on the material within or removed from, its natural environment or state. For example, a "recombinant nucleic acid" may refer to a nucleic acid that is made by recombining nucleic acids, for example, during cloning, DNA shuffling or other procedures, or by chemical or other mutagenesis; and a "recombinant polypeptide" or "recombinant protein" can refer to a polypeptide or protein which is produced by expression of a recombinant nucleic acid.

As used herein the term "engineered" includes manipulation of nucleic acid or polypeptide molecules by synthetic means, including, for example, recombinant techniques, in vitro peptide synthesis, enzymatic or chemical coupling of peptides or combinations thereof.

As used herein, the term "effective amount" or "therapeutically effective amount" refers to an amount of a therapeutic composition necessary or sufficient to realize a desired clinical outcome for a given condition and administration regimen, for example, an amount sufficient to achieve a concentration of a compound which is capable of preventing, reducing and/or treating influenza infection in a subject. Such amounts and concentrations can be determined by those skilled in the art and will typically be determined by a physician, in the light of the relevant circumstances, including, but not limited to, the condition to be treated, the chosen route of administration, the actual compound administered, the age, weight, and response of the individual patient, and the severity of the patient's symptoms.

As used herein, the term "therapeutic composition" refers to a compound or composition with a therapeutic use and includes, but is not limited to, biological compounds, such as antibodies, proteins and nucleic acids, as well as small organic molecule compounds that are chemically synthesized.

As used herein, the term "pharmaceutical composition" refers to a composition that includes a therapeutically effective amount of a therapeutic agent together with a pharmaceutically acceptable carrier and, if desired, one or more diluents or excipients. As used herein, the term "pharmaceutically acceptable" means that it is approved by a regulatory agency of a Federal or a state government or listed in the U.S. Pharmacopia, European Pharmacopia or other generally recognized pharmacopia for use in mammals, and more particularly in humans.

As used herein, the terms "treatment" or "treating" refer to both therapeutic treatment and prophylactic or preventative measures, wherein the object is to stabilize, prevent, alleviate or reduce one or more symptoms of influenza infection, or to delay, prevent, or inhibit progression of influenza infection. Treatment can also refer to clearance or reduction of an infectious agent such as influenza A virus in a subject, "Treatment" can also mean prolonging survival as compared to expected survival if not receiving treatment. Treatment need not mean that the infection is completely cured.

As use herein, the term "subject" or "patient" refers to any member of the subphylum cordata, including, but not limited to, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, and geese. The terms "mammals" and "animals" are included in this definition. Both adult and newborn mammals are intended to be covered.

As used herein, the term "neutralize" refers to the ability of an antibody, or antigen binding fragment thereof, to bind to an infectious agent, such as influenza A virus, and reduce the biological activity, for example, virulence, of the infectious agent. In one embodiment, the antibody or fragment thereof immunospecifically binds at least one specified epitope or antigenic determinant of the Influenza A virus. In a more particular embodiment, the antibody or fragment thereof immunospecifically binds at least one specified epitope or antigenic determinant of the Influenza A virus HA stalk protein.

An antibody can neutralize the activity of an infectious agent, such as Influenza A virus, at various points during the lifecycle of the virus. For example, an antibody may interfere with viral attachment to a target cell by interfering with the interaction of the virus and one or more cell surface receptors. Alternately, an antibody may interfere with one or more post-attachment interactions of the virus with its receptors, for example, by interfering with viral internalization by receptor-mediated endocytosis.

Anti-Influenza a Antibodies

Described herein are methods, compositions and articles of manufacture that include antibodies or fragments thereof that immunospecifically bind influenza A virus. In one embodiment, the antibody or fragment thereof immunospecifically binds at least one epitope specific to Influenza A virus. In a more particular embodiment, the antibody or fragment thereof immunospecifically binds an epitope on influenza A virus HA stalk protein. In one embodiment, the antibody or antigen binding fragment thereof is capable of binding to and/or neutralizing one or more group 1 subtype and one or more group 2 subtype of Influenza A virus, as described herein. In one embodiment, the antibody or antigen binding fragment thereof binds to an epitope that is conserved among at least H1, H2, H3, H4, H5, H6, H7, H8, H9, H10, H11, H12, H13, H14, H15, H16, H17, H18 or all influenza A HA subtypes. In another embodiment, the antibody or antigen binding fragment thereof binds to an epitope that is conserved among one or more, or at least 1, 2, 3, 4, 5, 6, 7, 8, 9, or 10 influenza A virus group 1 subtypes selected from H1, H2, H5, H6, H8, H9, H11, H12, H13 and H16 and one or more, or at least 1, 2, 3, 4, 5, or 6 group 2 subtypes selected from H3, H4, H7, H10, H14 and H15.

In one embodiment, the antibody or antigen binding fragment thereof binds at least H1, H2, H3, H4, H5, H6, H7, H8, H9, H10, H11, H12, H13, H14, H15, H16, H17 or H18 or all influenza A subtypes with an $EC_{50}$ of between about 0.01 ug/ml and about 5 ug/ml, or between about 0.01 ug/ml and about 0.5 ug/ml, or between about 0.01 ug/ml and about 0.1 ug/ml, or less than about 5 ug/ml, 1 ug/ml, 0.5 ug/ml, 0.1 ug/ml, or 0.05 ug/ml. In another embodiment, the antibody or antigen binding fragment thereof binds one or more, or at least 1, 2, 3, 4, 5, 6, 7, 8, 9, or 10 influenza A virus group 1 subtypes selected from H1, H2, H5, H6, H8, H9, H11, H12, H13 and H16 and one or more, or at least 1, 2, 3, 4, 5, or 6 group 2 subtypes selected from H3, H4, H7, H10, H14 and H15 with an $EC_{50}$ of between about 0.01 ug/ml and about 5 ug/ml, or between about 0.01 ug/ml and about 0.5 ug/ml, or between about 0.01 ug/ml and about 0.1 ug/ml, or less than about 5 ug/ml, 1 ug/ml, 0.5 ug/ml, 0.1 ug/ml, or 0.05 ug/ml. In one embodiment, the antibody binds one or more influenza A subtypes that have the potential to cause pandemics such as H2, H4, H5, H6, H7, and H9 with an $EC_{50}$ of between about 0.01 ug/ml and about 5 ug/ml, or between about 0.01 ug/ml and about 0.5 ug/ml, or between about 0.01 ug/ml and about 0.1 ug/ml, or less than about 5 ug/ml, 1 ug/ml, 0.5 ug/ml, 0.1 ug/ml, or 0.05 ug/ml. In one embodiment, the antibody binds seasonal H1N1 and H3N2 viruses with an $EC_{50}$ of between about 0.01 ug/ml and about 5 ug/ml, or between about 0.01 ug/ml and about 0.5 ug/ml, or between about 0.01 ug/ml and about 0.1 ug/ml, or less than about 5 ug/ml, 1 ug/ml, 0.5 ug/ml, 0.1 ug/ml, or 0.05 ug/ml.

In one embodiment, the antibody or antigen binding fragment thereof recognizes an epitope located in the stalk region of HA2. In a more particular embodiment, the antibody or antigen binding fragment binds to a conformational epitope in the conserved stalk region of HA2. In one embodiment, the epitope includes one or more amino acids selected from: positions 18, 19, 42, 45 in the stalk region of HA2 (positions are numbered according to H3 numbering system as described in Weiss et al., (1990) J. Mol. Biol. 212, 737-761) as contact residues. In a more particular embodiment, the epitope includes one or more amino acids selected from 18, 19, 42 and 45 in the stalk region of HA2 as contact residues. In a further embodiment, the epitope includes amino acids 18, 19, 42 and 45 in the stalk region of HA2 as contact residues. In yet a further embodiment, the epitope includes amino acids 18, 19, and 42 in the stalk region of HA2 as contact residues.

In one embodiment, the antibody or antigen binding fragment thereof neutralizes the activity of Influenza A by inhibiting the pH induced conformational change required for HA mediated fusion between viral and endosomal membranes. In another embodiment, the antibody or antigen binding fragment thereof neutralizes the activity of influenza A by inhibiting protease cleavage of the HA0 protein into HA1 and HA2 subunits, thereby interfering with the accessibility of the fusion peptide. In another embodiment, the antibody or antigen binding fragment thereof inhibits cell-to-cell transmission of influenza A virus.

In other embodiments, the antibody or antigen binding fragment can reduce the activity of influenza A virus infection by clearing the virus. In one embodiment, the antibody or antigen binding fragment can clear the virus via one or more Fc-effector functions, including, for example, ADCC, ADCP, and CDC.

In one embodiment, antibodies that specifically bind influenza A virus are described in U.S. Provisional Application Nos. 61/885,808, filed Oct. 2, 2013 and 62/002,414, filed May 23, 2014, and PCT Application No. PCT/US2014/058652, filed Oct. 1, 2014. Each of these disclosures is hereby incorporated by reference herein in its entirety.

MEDI8852

In one embodiment, the anti-influenza A antibody includes MEDI8852, a human IgG1 kappa monoclonal antibody (mAb) that binds to the conserved stalk region of the influenza HA protein and is capable of binding and/or neutralizing a large panel of flu viruses.

In one embodiment, the antibody includes a VH and/or VL that has at least a recited percent identity to at least one of the VH and/or VL sequences of MEDI8852. In one embodiment, the antibody includes a VH amino acid sequence having at least 75%, 80%, 85%, 90%, 95% or 100% identity to the VH amino acid sequence of SEQ ID NO: 2. In another embodiment, the antibody includes a VH amino acid sequence having at least 90%, 91%, 92%, 93%, 94%, 95%, 96%, 97%, 98%, 99% or 100% identity to the VH amino acid sequence of SEQ ID NO: 2. In another embodiment, the antibody includes a VL amino acid sequence having at least 75%, 80%, 85%, 90%, 95% or 100% identity to the VL amino acid sequence of SEQ ID NO:7. In another embodiment, the antibody includes a VL amino acid sequence having at least, 90%, 91%, 92%, 93%, 94%, 95%, 96%, 97%, 98%, 99% or having 100% identity to the VL amino acid sequence of SEQ ID NO:7. In one embodiment, the antibody includes a VH amino acid sequence having at least 75%, 80%, 85%, 90%, 95% or 100% identity to the VH amino acid sequence of SEQ ID NO: 2 and a VL amino acid sequence having at least 75%, 80%, 85%, 90%, 95% or 100% identity to the VL amino acid sequence of SEQ ID NO:7. In another embodiment; the antibody includes a VH amino acid sequence having at least 90%, 91%, 92%, 93%, 94%, 95%, 96%, 97%, 98%, 99% or 100% identity to the VH amino acid sequence of SEQ ID NO: 2 and a VL amino acid sequence having at least; 90%, 91%, 92%, 93%, 94%, 95%, 96%, 97%, 98%, 99% or having 100% identity to the VL amino acid sequence of SEQ ID NO:7.

Complementarity Determining Regions (CDRs)

While the variable domain (VH and VL) includes the antigen-binding region; the variability is not evenly distributed throughout the variable domains of antibodies. It is concentrated in segments called Complementarity Determining Regions (CDRs), both in the light chain (VL or VK) and the heavy chain (VH) variable domains. The more highly conserved portions of the variable domains are called the framework regions (FR). The variable domains of native heavy and light chains each include four FR, largely adopting a β-sheet configuration, connected by three CDRs, which form loops connecting, and in some cases forming part of, the β-sheet structure. The CDRs in each chain are held together in close proximity by the FR and, with the CDRs from the other chain, contribute to the formation of the antigen-binding site of antibodies. The three CDRs of the heavy chain are designated HCDR1, HCDR2, and HCDR3, and the three CDRs of the light chain are designated LCDR1, LCDR2, and LCDR3. Using the Kabat numbering system, HCDR1 begins at approximately amino acid 31 (i.e., approximately 9 residues after the first cysteine residue), includes approximately 5-7 amino acids, and ends at the next tyrosine residue. HCDR2 begins at the fifteenth residue after the end of HCDR1, includes approximately 16-19 amino acids, and ends at the next arginine or lysine residue.

HCDR3 begins at approximately the thirty third amino acid residue after the end of HCDR2; includes 3-25 amino acids; and ends at the sequence W-G-X-G, where X is any amino acid. LCDR1 begins at approximately residue 24 (i.e., following a cysteine residue); includes approximately 10-17 residues; and ends at the next tyrosine residue. LCDR2 begins at approximately the sixteenth residue after the end of LCDR1 and includes approximately 7 residues, LCDR3 begins at approximately the thirty third residue after the end of LCDR2; includes approximately 7-11 residues and ends at the sequence F-G-X-G, where X is any amino acid. CDRs vary considerably from antibody to antibody and, by definition, will not exhibit homology with the Kabat consensus sequences.

In one embodiment, the anti-influenza A antibody includes one or more heavy chain CDRs having at least 75%, 80%, 85%, 90%, 91%, 92%, 93%, 94%, 95%, 96%, 97%, 98%, 99% or 100% identity to a heavy chain CDR selected from HCDR1 (SEQ ID NO:3), HCDR2 (SEQ ID NO:4), and HCDR3 (SEQ ID NO:5). In another embodiment, the anti-influenza A antibody includes one or more light chain CDRs having at least 75%, 80%, 85%, 90%, 91%, 92%, 93%, 94%, 95%, 96%, 97%, 98%, 99% or 100% identity to a light chain CDR selected from LCDR1 (SEQ ID NO:8), LCDR1 (SEQ ID NO:9), and LCDR1 (SEQ ID NO:10). In one embodiment, the anti-influenza A antibody includes one or more heavy chain CDRs having at least 75%, 80%, 85%, 90%, 91%, 92%, 93%, 94%, 95%, 96%, 97%, 98%, 99% or 100% identity to a heavy chain CDR selected from HCDR1 (SEQ ID NO:3), HCDR2 (SEQ ID NO:4), and HCDR3 (SEQ ID NO:5) and one or more light chain CDRs having at least 75%, 80%, 85%, 90%, 91%, 92%, 93%, 94%, 95%, 96%, 97%, 98%, 99% or 100% identity to a light chain CDR selected from LCDR1 (SEQ ID NO:8), LCDR1 (SEQ ID NO:9), and LCDR1 (SEQ ID NO:10).

Framework Regions

The variable domains of the heavy and light chains each include four framework regions (FR1, FR2, FR3, FR4), which are the more highly conserved portions of the variable domains. The four FRs of the heavy chain are designated FR-H1, FR-H2, FR-H3 and FR-H4, and the four FRs of the light chain are designated FR-L1, FR-L2, FR-L3 and FR-L4. Using the Kabat numbering system, FR-H1 begins at position 1 and ends at approximately amino acid 30, FR-H2 is approximately from amino acid 36 to 49, FR-H3 is approximately from amino acid 66 to 94 and FR-H4 is approximately amino acid 103 to 113. FR-L1 begins at amino acid 1 and ends at approximately amino acid 23, FR-L2 is approximately from amino acid 35 to 49, FR-L3 is approximately from amino acid 57 to 88 and FR-L4 is approximately from amino acid 98 to 107. In certain embodiments the framework regions may contain substitutions according to the Kabat numbering system, e.g., insertion at 106A in FR-L1.

In addition to naturally occurring substitutions, one or more alterations, for example, one or more substitutions of FR residues may also be introduced in an antibody to improve or optimize binding affinity of the antibody for Influenza A virus. Examples of framework region residues to modify include those which non-covalently bind antigen directly (Amit et al., (1986) Science, 233:747-753); interact with/effect the conformation of a CDR (Chothia et al., (1987) J. Mol. Biol., 196:901-917); and/or participate in the VL-VH interface (U.S. Pat. No. 5,225,539).

Whereas mutations in CDR regions may improve affinity and function, mutations in framework regions may increase the risk of immunogenicity. This risk can be reduced by reverting framework mutations to germline, without adversely impacting the activity of the antibody. In one embodiment, the FR may include one or more amino acid changes for the purposes of "germlining." In germlining, the amino acid sequences of selected antibody heavy and light chains are compared to germline heavy and light chain amino acid sequences and certain framework residues of the selected VL and/or VH chains that differ from the germline configuration are "back-mutated" to germline configuration, such that the framework amino acid sequences are changed back to the same as the germline framework amino acid sequences. Such "back-mutation" or "germlining" of framework residues can be accomplished by standard molecular biology methods for introducing specific mutations; including, but not limited to, site-directed mutagenesis and PCR-mediated mutagenesis.

Nucleotide Sequences

In another embodiment, nucleotide sequences corresponding to the amino acid sequences and encoding antibodies described herein are provided. Thus; polynucleotide sequences encoding VH and VL regions, including CDRs and FRs of antibodies described herein, as well as expression vectors for their efficient expression in cells are provided.

In one embodiment, the polynucleotide encodes a VH amino acid sequence having at least 75%, 80%, 85%, 90%, 95% or 100% identity to the VH amino acid sequence of SEQ ID NO: 2. In another embodiment, the polynucleotide includes a VH amino acid sequence having at least 90%, 91%, 92%, 93%, 94%, 95%, 96%, 97%, 98%, 99% or 100% identity to the VH amino acid sequence of SEQ ID NO: 2. In one embodiment, the polynucleotide has a nucleic acid sequence with at least 75%, 80%, 85%, 90%, 95% or 100% identity to the nucleic acid sequence of SEQ ID NO: 1. In another embodiment, the polynucleotide has a nucleic acid sequence with at least 90%, 91%, 92%, 93%, 94%, 95%, 96%, 97%, 98%, 99% or 100% identity to the nucleic acid sequence of SEQ ID NO: 1.

In another embodiment, the polynucleotide encodes a VL amino acid sequence having at least 75%, 80%, 85%, 90%, 95% or 100% identity to the VL amino acid sequence of SEQ ID NO:7. In another embodiment, the polynucleotide encodes a VL amino acid sequence having at least, 90%, 91%, 92%, 93%, 94%, 95%, 96%, 97%, 98%, 99% or having 100% identity to the VL amino acid sequence of SEQ ID NO:7. In one embodiment, the polynucleotide has a nucleic acid sequence with at least 75%, 80%, 85%, 90%, 95% or 100% identity to the nucleic acid sequence of SEQ ID NO: 6. In another embodiment, the polynucleotide has a nucleic acid sequence with at least 90%, 91%, 92%, 93%, 94%, 95%, 96%, 97%, 98%, 99% or 100% identity to the nucleic acid sequence of SEQ ID NO: 6.

In one embodiment, the polynucleotide encodes a VH amino acid sequence having at least 75%, 80%, 85%, 90%, 95% or 100% identity to the VH amino acid sequence of SEQ ID NO: 2 and a VL amino acid sequence having at least 75%, 80%, 85%, 90%, 95% or 100% identity to the VL amino acid sequence of SEQ ID NO:7. In another embodiment, the polynucleotide includes a VH amino acid sequence having at least 90%, 91%, 92%, 93%, 94%, 95%, 96%, 97%, 98%, 99% or 100% identity to the VH amino acid sequence of SEQ ID NO: 2 and at least, 90%, 91%, 92%, 93%, 94%, 95%, 96%, 97%, 98%, 99% or having 100% identity to the VL amino acid sequence of SEQ ID NO:7.

The invention also encompasses polynucleotides that hybridize under stringent or lower stringency hybridization conditions, as defined herein, to polynucleotides that encode an antibody or antigen binding fragment thereof described herein.

Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 65° C., or any other stringent hybridization conditions known to those skilled in the art (see, for example, Ausubel, F. M. et al., eds. (1989) Current Protocols in Molecular Biology, vol. 1, Green Publishing Associates, Inc. and John Wiley and Sons, Inc., NY at pages 6.3.1 to 6.3.6 and 2.10.3).

Substantially identical sequences include polymorphic sequences, (i.e., alternative sequences or alleles in a population). An allelic difference may be as small as one base pair. Substantially identical sequences may also include mutagenized sequences, including sequences that include silent mutations. A mutation may include one or more residue changes, a deletion of one or more residues, or an insertion of one or more additional residues.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (see, for example, Kutmeier et al., (1994) BioTechniques 17:242). Briefly, overlapping oligonucleotides containing portions of the sequence encoding the antibody are synthesized, annealed, ligated and then amplified by PCR.

A polynucleotide encoding an antibody may also be generated from nucleic acids from a suitable source. If a clone containing a nucleic acid encoding a particular antibody is not available, but the sequence of the antibody molecule is known, a nucleic acid encoding the immunoglobulin may be chemically synthesized or obtained from a suitable source such as an antibody cDNA library, or a cDNA library generated from, or nucleic acid, for example, polyA+RNA, isolated from, any tissue or cells expressing the antibody, such as hybridoma cells selected to express an antibody, for example by PCR amplification using synthetic primers hybridizable to the 3' and 5' ends of the sequence or by cloning using an oligonucleotide probe specific for the particular gene sequence to identify a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods known in the art, including, but not limited to, recombinant DNA techniques, site directed mutagenesis, and PCR to generate antibodies having a different amino acid sequence, for example to create amino acid substitutions, deletions, and/or insertions. (see, for example, the techniques described in Sambrook et al., (1990), Molecular Cloning, A Laboratory Manual, 2d Ed., Cold Spring Harbor Laboratory, Cold Spring Harbor, N.Y. and Ausubel et al., eds., (1998) Current Protocols in Molecular Biology, John Wiley & Sons, NY).

Binding Characteristics

As described above, the anti-influenza A antibodies or antigen binding fragments thereof immunospecifically bind at least one specified epitope or antigenic determinant of the influenza A virus. In a more particular embodiment, the anti-influenza A antibody or antigen binding fragment thereof bind at least one specified epitope or antigenic determinant of the influenza A virus HA stalk protein, peptide, subunit, fragment, portion or any combination thereof either exclusively or preferentially with respect to other polypeptides.

Binding assays can be performed to determine binding characteristics of an antibody, including, but not limited to, direct binding assays or competition-binding assays. In one embodiment, binding can be detected using a standard ELISA or Flow Cytometry assay. In a direct binding assay, a candidate antibody is tested for binding to its cognate antigen. In a competition-binding assay, the ability of a candidate antibody to compete with a known antibody or other compound that binds to the influenza A virus HA stalk is assessed. In general, any method that permits the binding of an antibody with the influenza A virus HA stalk that can be detected can be used for detecting and measuring the binding characteristics of an antibody.

Determining the affinity constant and specificity of binding between antigen and antibody can be helpful in ascertaining the efficacy of prophylactic, therapeutic, diagnostic and research methods using the antibody or fragment thereof. "Binding affinity" generally refers to the strength of the sum total of the noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the equilibrium dissociation constant (Kd), which is calculated as the ratio $k_{off}/k_{on}$. (See, Chen et al., (1999) J. Mol Biol 293:865-881). Low-affinity antibodies generally bind antigen slowly and tend to dissociate readily, whereas high-affinity antibodies generally bind antigen faster and tend to remain bound longer. Methods and reagents suitable for determination of binding characteristics of an antibody are known in the art and/or are commercially available (See, for example, U.S. Pat. Nos. 6,849,425; 6,632,926; 6,294,391; 6,143,574). Moreover, equipment and software designed for such kinetic analyses are commercially available (e.g. Biacore® A100, and Biacore® 2000 instruments; Biacore International AB, Uppsala, Sweden).

In one embodiment, antibodies of the present invention, including binding fragments or variants thereof, may also be described or specified in terms of their binding affinity for influenza A virus. Typically, antibodies with high affinity have Kd of less than $10^{-7}$ M. In one embodiment, antibodies or binding fragments thereof bind influenza A virus, or fragments or variants thereof, with a dissociation constant or Kd of less than or equal to $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M or $10^{-15}$ M. In a more particular embodiment, antibodies or binding fragments thereof bind influenza A virus, or fragments or variants thereof, with a dissociation constant or Kd of less than or equal to $5\times10^{-10}$ M, $10^{-10}$ M, $5\times10^{-11}$ M, $10^{-11}$M, $5\times10^{-12}$M or $10^{-12}$M. The invention encompasses antibodies that bind influenza A virus with a dissociation constant or Kd that is within a range between any of the individual recited values.

In another embodiment, antibodies or binding fragments thereof bind influenza A virus or fragments or variants thereof with an off rate ($k_{off}$) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$, $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-5}$ sec$^{-1}$, $10^{-6}$ sec$^{-1}$, $5\times10^{-7}$ sec$^{-1}$ or $10^{-7}$ sec$^{-1}$. In a more particular embodiment, antibodies or binding fragments thereof bind influenza A virus or fragments or variants thereof with an off rate ($k_{off}$) less than or equal to $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-7}$ sec$^{-1}$ or $10^{-7}$ sec$^{-1}$. The invention also encompasses antibodies that bind influenza A virus with an off rate ($k_{off}$) that is within a range between any of the individual recited values.

In another embodiment, antibodies or binding fragments thereof bind influenza A virus or fragments or variants thereof with an on rate ($k_{on}$) of greater than or equal to $10^3$ M$^{-1}$ sec$^{-1}$, $5\times10^3$ M$^{-1}$ sec$^{-1}$, $10^4$M$^{-1}$ sec$^{-1}$, $5\times10^4$ M$^{-1}$ sec$^{-1}$, $10^5$M$^{-1}$ sec$^{-1}$, $5\times10^5$ sec$^{-1}$, $10^6$ M$^{-1}$ sec-1, $5\times10^6$ M$^{-1}$ sec$^{-1}$, $10^7$ M$^{-1}$ sec-1, or $5\times10^7$ M$^{-1}$ sec$^{-1}$. In a more particular embodiment, antibodies or binding fragments thereof bind influenza A virus or fragments or variants thereof with an on rate ($k_{on}$) greater than or equal to $10^5$ M$^{-1}$ sec$^{-1}$, $5\times10^5$ M$^{-1}$ sec$^{-1}$, $10^6$ M$^{-1}$ sec-1, $5\times10^6$ M$^{-1}$ sec$^{-1}$, $10^7$ M$^{-1}$ sec$^{-1}$ or $5\times10^7$ M$^{-1}$ sec$^{-1}$. The invention encompasses antibodies that bind influenza A virus with on rate ($k_{on}$) that is within a range between any of the individual recited values.

In one embodiment, the antibody or antigen binding fragment thereof immunospecifically binds to influenza A virus HA stalk and is capable of neutralizing influenza A virus infection. Neutralization assays can be performed using methods known in the art. The term "inhibitory concentration 50%" (abbreviated as "IC$_{50}$") represents the concentration of an inhibitor (e.g., an antibody) that is required for 50% neutralization of influenza A virus. It will be understood by one of ordinary skill in the art that a lower IC$_{50}$ value corresponds to a more potent inhibitor.

In one embodiment, an antibody or antigen binding fragment thereof according to the invention has a neutralizing potency expressed as 50% inhibitory concentration (IC$_{50}$ ug/ml) in the range of from about 0.01 ug/ml to about 50 ug/ml, or in the range of from about 0.01 ug/ml to about 5 ug/ml of antibody, or in the range of from about 0.01 ug/ml to about 0.1 ug/ml of antibody for neutralization of influenza A virus in a microneutralization assay.

In certain embodiments, the antibodies described herein may induce cell death. An antibody or antigen binding fragment thereof which "induces cell death" is one which causes a viable cell to become nonviable. In one embodiment, the antibodies or fragments thereof described herein may induce cell death via ADCC, CDC, and/or ADCP. Assays for measuring ADCC, CDC and ADCP are known.

In one embodiment, the antibody or fragment thereof induces cell death via apoptosis. An antibody or fragment thereof which "induces apoptosis" is one which induces programmed cell death as determined by binding of annexin V, fragmentation of DNA, cell shrinkage, dilation of endoplasmic reticulum, cell fragmentation; and/or formation of membrane vesicles (called apoptotic bodies). Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

Production of Antibodies

The following describes techniques for the production of the antibodies and fragments thereof as described herein.

Monoclonal Antibodies

Monoclonal antibodies can be prepared using a wide variety of techniques known in the art, including the use of hybridoma (Kohler et al., (1975) Nature, 256:495; Harlow et al., (1988) Antibodies: A Laboratory Manual, (Cold Spring Harbor Laboratory Press, 2nd ed.); Hammerling et al., (1981) in: Monoclonal Antibodies and T-Cell Hybridomas 563-681 (Elsevier, N.Y.), recombinant, and phage display technologies, or a combination thereof. The term "monoclonal antibody," as used herein, refers to an antibody obtained from a population of substantially homogeneous or isolated antibodies, wherein the individual antibodies that make up the population are identical except for possible naturally occurring mutations that may be present in minor amounts. Monoclonal antibodies are highly specific, and are directed against a single antigenic site. Furthermore, in contrast to polyclonal antibody preparations; which include different antibodies directed against different determinants (epitopes), each monoclonal antibody is directed against the same determinant on the antigen. In addition to their specificity, monoclonal antibodies are advantageous in that they may be synthesized uncontaminated by other antibodies. The modifier "monoclonal" is not to be construed as requiring production of the antibody by any particular method. Following is a description of representative methods for producing monoclonal antibodies which is not intended to be limiting and may be used to produce, for example, monoclonal mammalian, chimeric, humanized, human, domain, diabodies, vaccibodies, linear and multispecific antibodies.

Hybridoma Techniques

Methods for producing and screening for specific antibodies using hybridoma technology are routine and well known in the art. In the hybridoma method, mice or other appropriate host animals, such as hamster, are immunized to elicit lymphocytes that produce or are capable of producing antibodies that will specifically bind to the antigen used for immunization. Alternatively, lymphocytes may be immunized in vitro. After immunization, lymphocytes are isolated and then fused with a myeloma cell line using a suitable fusing agent or fusion partner, such as polyethylene glycol, to form a hybridoma cell (Goding, (1986) Monoclonal Antibodies: Principles and Practice, pp. 59-103 (Academic Press). In certain embodiments, the selected myeloma cells are those that fuse efficiently, support stable high-level production of antibody by the selected antibody-producing cells, and are sensitive to a selective medium that selects against the unfused parental cells. In one aspect, the myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, J, (1984) Immunol., 133:3001; and Brodeur et al., (1987) Monoclonal Antibody Production Techniques and Applications, pp. 51-63 (Marcel Dekker, Inc., New York).

Once hybridoma cells that produce antibodies of the desired specificity, affinity, and/or activity are identified, the clones may be subcloned by limiting dilution procedures and grown by standard methods. Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the sub-clones can be separated from the culture medium, ascites fluid, or serum by conventional antibody purification procedures include, but are not limited to, affinity chromatography (e.g., using protein A or protein G-Sepharose) or ion-exchange chromatography, affinity tags, hydroxylapatite chromatography, gel electrophoresis, and dialysis.

Recombinant DNA Techniques

Methods for producing and screening for specific antibodies using recombinant DNA technology are routine and well known in the art. DNA encoding a monoclonal antibody or fragment thereof may be readily isolated and/or sequenced using conventional procedures. Once isolated, the DNA may be placed into expression vectors, which can be transfected into host cells such as E, coil cells, simian COS cells, Chinese Hamster Ovary (CHO) cells, or myeloma cells that do not otherwise produce antibody protein, to obtain the synthesis of monoclonal antibodies in the recombinant host cells.

Recombinant expression of an antibody or variant thereof generally requires construction of an expression vector containing a polynucleotide that encodes the antibody. Thus, provided herein are replicable vectors that include a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule and the variable domain of the antibody may be cloned into such a vector for expression of the entire heavy, the entire light chain, or both the entire heavy and light chains.

Once the expression vector is transferred to a host cell by conventional techniques, the transfected cells can be cultured by conventional techniques to produce an antibody. Thus, provided herein are host cells containing a polynucleotide encoding an antibody described herein or fragments thereof, or a heavy or light chain thereof, or portion thereof, or a single-chain antibody, operably linked to a heterologous promoter. In certain embodiments for the expression of double-chained antibodies, vectors encoding both the heavy and light chains may be co-expressed in the host cell for expression of the entire immunoglobulin molecule.

Mammalian cell lines available as hosts for expression of recombinant antibodies are well known in the art and include many immortalized cell lines available from the American Type Culture Collection (ATCC), including, but not limited to, Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, MACK, 293, 3T3, W138, BT483, Hs578T, HTB2, BT2O and T47D, NSO (a murine myeloma cell line that does not endogenously produce any functional immunoglobulin chains), SP20, CRL7O3O and HsS78Bst cells. Human cell lines developed by immortalizing human lymphocytes can be used to recombinantly produce monoclonal antibodies. The human cell line PER.C6. (Crucell, Netherlands) can be used to recombinantly produce monoclonal antibodies.

Additional cell lines which may be used as hosts for expression of recombinant antibodies include, but are not limited to, insect cells (e.g. Sf21/Sf9, *Trichoplusia ni* Bti-Tn5b1-4) or yeast cells (e.g. *S. cerevisiae, Pichia*, U.S. Pat. No. 7,326,681; etc), plants cells; and chicken cells.

In certain embodiments, antibodies and fragments thereof described herein can be stably expressed in a cell line. Stable expression can be used for long-term, high-yield production of recombinant proteins. Host cells can be transformed with an appropriately engineered vector that includes expression control elements, including, but not limited to, promoter, enhancer, transcription terminators, and polyadenylation sites, and a selectable marker gene. Following the introduction of the foreign DNA, cells may be allowed to grow for 1-2 days in an enriched media, and then are switched to a selective media. The selectable marker in the recombinant plasmid confers resistance to the selection and allows cells that stably integrated the plasmid into their chromosomes to grow and form foci which in turn can be cloned and expanded into cell lines. Methods for producing stable cell lines with a high yield are well known in the art and reagents are generally available commercially.

In certain embodiments, antibodies and fragments thereof described herein are transiently expressed in a cell line. Transient transfection is a process in which the nucleic acid introduced into a cell does not integrate into the genome or chromosomal DNA of that cell. It is in fact maintained as an extra-chromosomal element, for example, as an episome, in the cell. Transcription processes of the nucleic acid of the episome are not affected and a protein encoded by the nucleic acid of the episome is produced.

The cell line, either stably or transiently transfected, is maintained in cell culture medium and conditions well known in the art for expression and production of monoclonal antibodies. In certain embodiments, the mammalian cell culture media is based on commercially available media formulations, including, for example, DMEM or Ham's F12. In other embodiments, the cell culture media is modified to support increases in both cell growth and biologic protein expression. As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium may be modified for a specific cell culture use, including, for example, cell culture growth medium which is formulated to promote cellular growth, or cell culture production medium which is formulated to promote recombinant protein production. The terms nutrient, ingredient, and component are used interchangeably herein to refer to the constituents that make up a cell culture medium.

In one embodiment, the cell lines are maintained using a fed batch method. As used herein, "fed batch method," refers to a method by which a fed batch cell culture is supplied with additional nutrients after first being incubated with a basal medium. For example, a fed batch method may include adding supplemental media according to a determined feeding schedule within a given time period. Thus, a "fed batch cell culture" refers to a cell culture wherein the cells, typically mammalian, and culture medium are supplied to the culturing vessel initially and additional culture nutrients are fed, continuously or in discrete increments, to the culture during culturing, with or without periodic cell and/or product harvest before termination of culture.

Suitable cell culture medium and the nutrients contained therein are known to one of skill in the art. In one embodiment, the cell culture medium includes a basal medium and at least one hydrolysate, e.g., soy-based hydrolysate, a yeast-based hydrolysate, or a combination of the two types of hydrolysates resulting in a modified basal medium. In another embodiment, the additional nutrients may include only a basal medium, such as a concentrated basal medium, or may include only hydrolysates, or concentrated hydrolysates. Suitable basal media include, but are not limited to Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (see, e.g., CHO protein free medium (Sigma) or EX-CELL™ 325 PF CHO Serum-Free Medium for CHO Cells Protein-Free (SAFC Bioscience), and Iscove's Modified Dulbecco's Medium. Other examples of basal media include BME Basal Medium (Gibco-Invitrogen; see also Eagle, H (1965) Proc. Soc. Exp. Biol. Med. 89, 36); Dulbecco's Modified Eagle Medium (DMEM, powder) (Gibco-Invitrogen (#31600); see also Dulbecco and Freeman (1959) Virology 8:396; Smith et al., (1960) Virology 12:185. Tissue Culture Standards Committee. In Vitro 6:2, 93); CMRL 1066 Medium (Gibco-Invitrogen (#11530); see also Parker et al., (1957) Special Publications, N.Y, Academy of Sciences, 5:303).

The basal medium may be serum-free, meaning that the medium contains no serum (e.g., fetal bovine serum (FBS), horse serum, goat serum, or any other animal-derived serum known to one skilled in the art) or animal protein free media or chemically defined media.

The basal medium may be modified in order to remove certain non-nutritional components found in standard basal medium, such as various inorganic and organic buffers, surfactant(s), and sodium chloride. Removing such components from basal cell medium allows an increased concentration of the remaining nutritional components, and may improve overall cell growth and protein expression. In addition, omitted components may be added back into the cell culture medium containing the modified basal cell medium according to the requirements of the cell culture conditions. In certain embodiments, the cell culture medium contains a modified basal cell medium, and at least one of the following nutrients: an iron source, a recombinant growth factor, a buffer, a surfactant, an osmolarity regulator, an energy source, and non-animal hydrolysates. In addition, the modified basal cell medium may optionally contain amino acids, vitamins, or a combination of both amino acids and vitamins. In another embodiment, the modified basal medium further contains glutamine, e.g., L-glutamine, and/or methotrexate.

Antibody production can be conducted in large quantities in a bioreactor using fed-batch, batch, perfusion or continuous feed bioreactor methods known in the art. Large-scale bioreactors have at least 1000 liters of capacity, for example, about 1,000 to 100,000 liters of capacity. Small scale bioreactors refers generally to cell culturing in no more than approximately 100 liters in volumetric capacity, and can range from about 1 liter to about 100 liters. Alternatively, single-use bioreactors (SUB) may be used for either large-scale or small-scale culturing.

Temperature, pH, agitation, aeration and inoculum density will vary depending upon the host cells used and the recombinant protein to be expressed. For example, a recombinant protein cell culture may be maintained at a temperature between 30 and 45° C., The pH of the culture medium may be monitored during the culture process such that the pH stays at a desired level, which may be for certain host cells, within a pH range of 6.0 to 8.0.

Phage Display Techniques

Monoclonal antibodies or antibody fragments can be isolated from antibody phage libraries generated using the techniques described in McCafferty et al., (1990) Nature, 348:552-554. Clackson et al., (1991) Nature, 352:624-628 and Marks et al., (1991) J. Mol. Biol., 222:581-597. Using such methods, antibodies can be isolated by screening a recombinant combinatorial antibody library, for example, a scFv phage display library, prepared using human VL and VH cDNAs prepared from mRNA derived from human lymphocytes. Methodologies for preparing and screening such libraries are known in the art.

In phage display methods, functional antibody domains are displayed on the surface of phage particles which carry the polynucleotide sequences encoding them. In a particular embodiment, phage can be utilized to display antigen-binding domains expressed from a repertoire or combinatorial antibody library (e.g.; human or murine). Phage expressing an antigen binding domain that binds the antigen of interest can be selected or identified using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein.

After phage selection, the antibody coding regions from the phage can be isolated and used to generate whole antibodies, including human antibodies, humanized antibodies, or any other desired antigen binding fragment, and expressed in any desired host, including mammalian cells, insect cells, plant cells, yeast, and bacteria.

Antibody Purification and Isolation

Once an antibody molecule has been produced by recombinant or hybridoma expression, it may be purified by any method known in the art for purification of an immunoglobulin molecule, for example, by chromatography, including but not limited to, ion exchange, affinity, particularly Protein A or Protein G affinity, and sizing column chromatography; centrifugation; differential solubility; or by any other standard technique for the purification of proteins. Further, the antibodies or fragments thereof may be fused to heterologous polypeptide sequences (referred to herein as "tags") to facilitate purification.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., (1992) Bio/Technology, 10:163-167 describe a procedure for isolating antibodies which are secreted into the periplasmic space of E. coli. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, ion exchange chromatography, gel electrophoresis, dialysis, and/or affinity chromatography either alone or in combination with other purification steps.

Human Antibodies

Human antibodies can be generated using methods well known in the art. Human antibodies avoid some of the problems associated with antibodies that possess murine or rat variable and/or constant regions, which can lead to rapid clearance of the antibody or fragment thereof or generation of an immune response against the antibody or fragment therefor.

Human antibodies can be derived by in vitro methods. Suitable examples include but are not limited to phage display (MedImmune (formerly CAT), Morphosys, Dyax, Biosite/Medarex, Xoma, Symphogen, Alexion (formerly Proliferon), Affimed) ribosome display (MedImmune (formerly CAT)), yeast display, and the like. Phage display technology can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. A repertoire of V genes from unimmunized human donors can be constructed and antibodies to a diverse array of antigens (including self-antigens) can be isolated essentially following the techniques described by Marks et al., (1991) J. Mol. Biol. 222:581-597, or Griffith et al., (1993) EMBO J. 12:725-734. Human antibodies may also be generated by in vitro activated B cells (see, U.S. Pat. Nos. 5,567,610 and 5,229,275)

Antibody Fragments

In certain embodiments, the antibodies of the invention include antibody fragments or antibodies that include such fragments. Typically; an antibody fragment includes a portion of the full length antibody, typically the antigen binding or variable region thereof. Examples of antibody fragments include Fab, Fab', F(ab')$_2$, Fd and Fv fragments, diabodies, linear antibodies and single-chain antibody molecules. In one embodiment, the antibody fragment includes an antigen binding fragment.

Traditionally, antibody fragments were derived via proteolytic digestion of intact antibodies using techniques well known in the art. However, antibody fragments can also be produced directly by recombinant host cells. Fab; Fv and scFv antibody fragments can all be expressed in and secreted from E. coli, thus allowing the facile production of large amounts of these fragments. In one embodiment, the antibody fragments can be isolated from the antibody phage libraries. Alternatively, Fab'-SH fragments can also be directly recovered from E. coli and chemically coupled to form F(ab')$_2$ fragments (Carter et al., (1992) Bio/Technology, 10:163-167). According to another approach, F(ab')$_2$ fragments can be isolated directly from recombinant host cell culture. Other techniques for the production of antibody fragments will be apparent to the skilled practitioner. In other embodiments, the antibody is a single-chain Fv fragment (scFv).

Antibody fragments can also include domain antibodies, e.g., antibodies containing the small functional binding units of antibodies, corresponding to the variable regions of the heavy (VH) or light (VL) chains of human antibodies and linear antibodies, which include a pair of tandem Fd segments (VH-CH1-VH-CH1) which form a pair of antigen-binding regions. (See, Zapata et al., (1995) Protein Eng., 8(10):1057-1062), Variant Fc Regions Variants in the Fc region can enhance or diminish effector function of the antibody and may alter the pharmacokinetic properties, for example, the half-life, of the antibody. Thus, in certain embodiments; the antibodies include an altered Fc region (also referred to herein as "variant Fc region") in which one or more alterations have been made in the Fc region in order to change functional and/or pharmacokinetic properties of the antibodies. Such alterations may result in a decrease or increase of Clq binding and CDC or of FcγR binding, for IgG, and ADCC, or ADCP. The present invention encompasses the antibodies described herein with variant Fc regions wherein changes have been made to fine tune the effector function, enhancing or diminishing, or providing a desired effector function. Antibodies that include a variant Fc region are also referred to here as "Fc variant antibodies." As used herein native refers to the unmodified parental sequence and the antibody that includes a native Fc region is herein referred to as a "native Fc antibody". Fc variant antibodies can be generated by methods well known to one skilled in the art. Non-limiting examples include, isolating antibody coding regions (e.g., from hybridoma) and making one or more desired substitutions in the Fc region. Alternatively, the antigen-binding portion or variable region of an antibody may be sub-cloned into a vector encoding a variant Fc region. In one embodiment, the variant Fc region exhibits a similar level of inducing effector function as compared to the native Fc region. In another embodiment, the variant Fc region exhibits a higher induction of effector function as compared to the native Fc. Methods for measuring effector function are well known in the art.

Modification of the Fc region, includes, but is not limited to, amino acid substitutions, amino acid additions, amino acid deletions and changes in post-translational modifications to Fc amino acids (e.g glycosylation) and may be used to fine tune the effector function.

The Fc region includes the constant region of an antibody excluding the first constant region immunoglobulin domain. Thus Fc refers to the last two constant region immunoglobulin domains of IgA, IgD, and IgG, and the last three constant region immunoglobulin domains of IgE and and the flexible hinge N-terminal to these domains. For IgA and IgM Fc may include the J chain. For IgG, Fc includes immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to include residues C226 or P230 to its carboxyl-terminus, wherein the numbering is according to the EU index as set forth in Kabat. Fc may refer to this region in isolation, or this region in the context of an antibody, antibody fragment, or Fc fusion protein. Polymorphisms have been observed at a number of different Fc positions, including but not limited to positions 270, 272, 312, 315, 356, and 358 as numbered by the EU index, and thus slight differences between the presented sequence and sequences in the prior art may exist.

In one embodiment, Fc variant antibodies exhibit altered binding affinity for one or more Fc receptors including, but not limited to FcRn, FcγR1 (CD64) including isoforms FcγRIA, FcγRIB, and FcγRIC; FcγRII (CD32 including isoforms FcγRIIA, FcγRIIB, and FcγRIIC); and FcγRIII (CD16, including isoforms FcγRIIIA and FcγRIIIB) as compared to an native Fc antibody.

Antibody effector functions include ADCC, a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing cells and subsequently kill the cells with cytotoxins. Specific high-affinity IgG antibodies directed to the surface of cells "arm" the cytotoxic cells and are required for such killing. Lysis of the cell is extracellular, requires direct cell-to-cell contact, and does not involve complement.

Another antibody effector function is CDC, which refers to a biochemical event of cell destruction by the complement system. The complement system is a complex system of proteins found in normal blood plasma that combines with antibodies to destroy pathogenic bacteria and other foreign cells.

Still another process encompassed by the term antibody effector function is ADCP, which refers to a cell-mediated reaction wherein nonspecific cytotoxic cells that express one or more effector ligands recognize bound antibody on a cell and subsequently cause phagocytosis of the cell.

In certain embodiments, an antibody that includes an Fc variant has enhanced cytotoxicity or phagocytosis activity (e.g., ADCC, CDC and ADCP) relative to an antibody that includes a native Fc region.

In certain embodiments, Fc variant antibodies exhibit decreased ADCC activities as compared to a native Fc antibody. In certain embodiments, Fc variant antibodies have no detectable ADCC activity. In specific embodiments, the reduction and/or ablatement of ADCC activity may be attributed to the reduced affinity Fc variant antibodies exhibit for Fc ligands and/or receptors.

In an alternative embodiment, Fc variant antibodies exhibit increased ADCC activities as compared to a native Fc antibody. In specific embodiments, the increased ADCC activity may be attributed to the increased affinity Fc variant antibodies exhibit for Fc ligands and/or receptors.

In one embodiment, an Fc variant antibody has enhanced binding to the Fc receptor FcγRIIIA and has enhanced ADCC activity relative to a native Fc antibody.

In certain embodiments, cytotoxicity is mediated by CDC and the Fc variant antibody has either enhanced or decreased CDC activity relative to a native Fc antibody. In one embodiment, antibodies described herein exhibit increased CDC activity as compared to a native Fc antibody. In specific embodiments, the increase of CDC activity may be attributed to the increased affinity Fc variant antibodies exhibit for C1q. Antibodies may exhibit increased CDC activity as compared to a native Fc antibody by virtue of COMPLEGENT® Technology (Kyowa Hakko Kirin Co., Ltd.), which enhances one of the major mechanisms of action of an antibody, CDC. With an approach called isotype chimerism, in which portions of IgG3, an antibody's isotype, are introduced into corresponding regions of IgG1, the standard isotype for therapeutic antibodies, COMPLEGENT® Technology significantly enhances CDC activity beyond that of either IgG1 or IgG3, while retaining the desirable features of IgG1, such as ADCC, PK profile and Protein A binding. In addition, it can be used together with POTELLIGENT® Technology, creating an even superior therapeutic Mab (ACCRETAMAB®) with enhanced ADCC and CDC activities In another embodiment, Fc variant antibodies may have enhanced ADCC activity and enhanced serum half-life relative to a native Fc antibody. In one embodiment, an Fc variant antibody may exhibit enhanced CDC activity and enhanced serum half-life relative to a native Fc antibody. In another embodiment, an Fc variant antibody may have enhanced ADCC activity, enhanced CDC activity and enhanced serum half-life relative to a native Fc antibody.

The serum half-life of proteins that include Fc regions may be increased by increasing the binding affinity of the Fc region for FcRn. The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body or a specific compartment thereof, for example, as measured in serum, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The increase in half-life allows for the reduction in amount of drug given to a patient as well as a reduction in frequency of administration. To increase the serum half-life of the antibody; a salvage receptor binding epitope may be incorporated into the antibody or fragment thereof. As used herein, the term "salvage receptor binding epitope" refers to an epitope of the Fc region of an IgG molecule (e.g.; IgG1, IgG2; IgG3, or IgG4) that is responsible for increasing the in vivo serum half-life of the IgG molecule.

Alternatively, antibodies with increased half-lives may be generated by modifying amino acid residues identified as involved in the interaction between the Fc and the FcRn receptor. In addition, the half-life of antibodies described herein may be increased by conjugation to PEG or Albumin by techniques widely utilized in the art.

In one embodiment, the present invention provides Fc variants, wherein the Fc region includes a modification (e.g., amino acid substitutions, amino acid insertions, amino acid deletions) at one or more positions selected from 221, 225, 228, 234, 235, 236, 237, 238, 239, 240, 241, 243, 244, 245, 247, 250, 251, 252, 254, 255, 256, 257, 262, 263, 264, 265, 266, 267, 268, 269, 279, 280, 284, 292, 296, 297, 298, 299, 305, 308, 313, 316, 318, 320, 322, 325, 326, 327, 328, 329, 330, 331, 332, 333, 334, 339, 341, 343, 370, 373, 378, 392, 416, 419, 421, 428, 433, 434, 435, 436, 440, and 443 as numbered by the EU index as set forth in Kabat. Optionally, the Fc region may include a modification at additional and/or alternative positions known to one skilled in the art.

In a specific embodiment, the present invention provides an Fc variant, wherein the Fc region includes at least one substitution selected from 221K, 221Y, 225E, 225K, 225W, 228P, 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235E, 235F, 236E, 237L, 237M, 237P, 239D, 239E, 239N, 239Q, 239F, 239T, 239H, 239Y, 240I, 240A, 240T, 240M, 241W, 241L, 241Y, 241E, 241R, 243W, 243L, 243Y, 243R, 243Q, 244H, 245A, 247L, 247V, 247G, 250E, 250Q, 251F, 252L, 252Y, 254S, 254T, 255L, 256E, 256F, 256M, 257C, 257M, 257N, 262I, 262A, 262T, 262E, 263I, 263A, 263T, 263M, 264L, 264I, 264W, 264T, 264R, 264F, 264M, 264Y, 264E, 265A, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 296G, 297S, 297D, 297E, 298A, 298H, 298I, 298T, 298F, 299I, 299L, 299A, 299S, 299V, 299H, 299F, 299E, 305I, 308F, 313F, 316D, 318A, 318S, 320A, 320S, 322A, 322S, 325Q, 325L, 325I, 325D, 325E, 325A, 325T, 325V, 325H, 326A, 326D, 326E, 326G, 326M, 326V, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 333A, 333D, 333G, 333Q, 333S, 333V, 334A, 334E, 334H, 334L, 334M, 334Q, 334V, 334Y, 339T, 370E, 370N, 378D, 392T, 396L, 416G, 419H, 421K, 428L, 428F, 433K, 433L, 434A, 424F, 434W, 434Y, 436H, 440Y and 443W as numbered by the EU index as set forth in Kabat. Optionally, the Fc region may include additional and/or alternative amino acid substitutions known to one skilled in the art.

In a specific embodiment, the present invention provides an Fc variant antibody, wherein the Fc region includes at least one modification (e.g., amino acid substitutions, amino acid insertions, amino acid deletions) at one or more positions selected from 228, 234, 235 and 331 as numbered by the EU index as set forth in Kabat. In one embodiment, the modification is at least one substitution selected from 228P, 234F, 235E, 235F, 235Y, and 331S as numbered by the EU index as set forth in Kabat.

In another specific embodiment, the present invention provides an Fc variant antibody, wherein the Fc region is an IgG4 Fc region and includes at least one modification at one or more positions selected from 228 and 235 as numbered by the EU index as set forth in Kabat. In still another specific embodiment, the Fc region is an IgG4 Fc region and the non-naturally occurring amino acids are selected from 228P, 235E and 235Y as numbered by the EU index as set forth in Kabat.

In another specific embodiment, the present invention provides an Fc variant, wherein the Fc region includes at least one non-naturally occurring amino acid at one or more positions selected from 239, 330 and 332 as numbered by the EU index as set forth in Kabat. In one embodiment, the modification is at least one substitution selected from 239D, 330L, 330Y, and 332E as numbered by the EU index as set forth in Kabat.

In a specific embodiment, the present invention provides an Fc variant antibody, wherein the Fc region includes at least one non-naturally occurring amino acid at one or more positions selected from 252, 254, and 256 as numbered by the EU index as set forth in Kabat. In one embodiment, the modification is at least one substitution selected from 252Y, 254T and 256E as numbered by the EU index as set forth in Kabat. In one embodiment, the modification includes three substitutions 252Y, 254T and 256E as numbered by the EU index as set forth in Kabat (known as "YTE").

In certain embodiments the effector functions elicited by IgG antibodies depend on the carbohydrate moiety linked to the Fc region of the protein (Claudia Ferrara et al., (2006) Biotechnology and Bioengineering 93:851-861). Thus, glycosylation of the Fc region can be modified to increase or decrease effector function. Accordingly, in one embodiment the Fc regions of antibodies include altered glycosylation of amino acid residues. In another embodiment, the altered glycosylation of the amino acid residues results in lowered effector function. In another embodiment, the altered glycosylation of the amino acid residues results in increased effector function. In one embodiment, the Fc region has reduced fucosylation. In another embodiment, the Fc region is afucosylated.

Addition of sialic acid to the oligosaccharides on IgG molecules can enhance their anti-inflammatory activity and alter cytotoxicity (Keneko et al., Science (2006) 313:670-673; Scallon et al., (2007) Mol. Immuno. 44(7):1524-34). In particular, IgG molecules with increased sialylation have anti-inflammatory properties whereas IgG molecules with reduced sialylation have increased immunostimulatory properties (e.g., increase ADCC activity). Therefore, an antibody can be modified with an appropriate sialylation profile for a particular therapeutic application. In one embodiment, the Fc regions of an antibody includes an altered sialylation profile compared to the native Fc region. In one embodiment, the Fc regions of antibodies include an increased sialylation profile compared to the native Fc region. In another embodiment, the Fc regions of antibodies include a decreased sialylation profile compared to the native Fc region. Other modifications and/or substitutions and/or additions and/or deletions of the Fc domain will be readily apparent to one skilled in the art.

Glycosylation

In one embodiment, the glycosylation pattern in the variable region of the present antibodies is modified to alter the affinity of the antibody for antigen. In one embodiment, the antibody is aglycoslated (i.e., the antibody lacks glycosylation). Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Furthermore, aglycosylated antibodies may be produced in bacterial cells which lack the necessary glycosylation machinery, Antibody Conjugates In another embodiment, the anti-influenza A antibody or fragment thereof is covalently attached to a moiety, and can be referred to as an antibody conjugate. Moieties suitable for attachment to the antibodies include, but are not limited to, proteins, peptides, drugs, labels, and cytotoxins and can be conjugated to the antibody or fragment thereof to alter or fine tune one or more characteristics (e.g., biochemical, binding and/or functional) of the antibody or fragment. Methods for forming conjugates, making amino acid and/or polypeptide changes and post-translational modifications are well known in the art.

In one embodiment, the attached substance is a therapeutic agent, a detectable label (also referred to herein as a reporter molecule) or a solid support. Suitable substances for attachment to antibodies include, but are not limited to, an amino acid, a peptide, a protein, a polysaccharide, a nucleoside, a nucleotide, an oligonucleotide, a nucleic acid, a hapten, a drug, a hormone, a lipid, a lipid assembly, a synthetic polymer, a polymeric microparticle, a biological cell, a virus, a fluorophore, a chromophore, a dye, a toxin, a hapten, an enzyme, an antibody, an antibody fragment, a radioisotope, solid matrixes, semi-solid matrixes and combinations thereof.

In certain embodiments, the antibodies are conjugated to a solid support. Antibodies may be conjugated to a solid support as part of the screening and/or purification and/or manufacturing process. Alternatively antibodies may be conjugated to a solid support as part of a diagnostic method or composition. A solid support suitable is typically substantially insoluble in liquid phases. A large number of supports are available and are known to one of ordinary skill in the art and include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and non-conducting metals, glass (including microscope slides) and magnetic supports. More specific examples of solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch. FICOLL, heparin, glycogen, amylopectin, mannan, inulin, nitrocellulose, diazocellulose, polyvinylchloride, polypropylene, polyethylene (including polyethylene glycol)), nylon, latex bead, magnetic bead, paramagnetic bead, superparamagnetic bead, and starch.

In some embodiments, the solid support may include a reactive functional group, including, but not limited to, hydroxyl, carboxyl, amino, thiol, aldehyde, halogen, nitro, cyano, amino, urea, carbonate, carbamate, isocyanate, sulfone, sulfonate, sulfonamide, and sulfoxide, for attaching the antibodies.

A suitable solid phase support can be selected on the basis of desired end use and suitability for various synthetic protocols. For example, where amide bond formation is desirable to attach the antibodies to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

In certain embodiments, the antibody or fragment thereof is conjugated to a label for diagnostics or other assays wherein the antibody and/or its associated ligand may be detected. Labels include, without limitation, a chromophore, a fluorophore, a fluorescent protein, a phosphorescent dye, a tandem dye, a particle, a hapten, an enzyme and a radioisotope.

In certain embodiments, the antibodies are conjugated to a fluorophore, including but not limited to, a pyrene, an anthracene, a naphthalene, an acridine, a stilbene, an indole or benzindole, an oxazole or benzoxazole, a thiazole or benzothiazole, a 4-amino-7-nitrobenz-2-oxa-1, 3-diazole (NBD), a cyanine, a carbocyanine, a carbostyryl, a porphyrin, a salicylate, an anthranilate, an azulene, a perylene, a pyridine, a quinoline, a borapolyazaindacene; a xanthene, an oxazine, a benzoxazine, a carbazine, a phenalenone, a coumarin, a benzofuran; a benzphenalenone; and derivatives thereof. As used herein, oxazines include resorufins, aminooxazinones, diaminooxazines, and their benzo-substituted analogs.

In a specific embodiment, the fluorophores include xanthene (rhodol, rhodamine, fluorescein and derivatives thereof) coumarin, cyanine, pyrene, oxazine and borapolyazaindacene. In other embodiments, such fluorophores are sulfonated xanthenes, fluorinated xanthenes, sulfonated coumarins, fluorinated coumarins and sulfonated cyanines. Also included are dyes sold under the tradenames, and generally known as, ALEXA FLUOR®, DyLight, CY® Dyes, BODIPY®, OREGON GREEN®, PACIFIC BLUE™, IRDYE®, FAM, FITC, and ROX™.

The choice of the fluorophore attached to the antibody will determine the absorption and fluorescence emission properties of the conjugated antibody. Physical properties of a fluorophore label that can be used for antibody and antibody bound ligands include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. In certain embodiments, the fluorophore has an absorption maximum at wavelengths greater than 480 nm. In other embodiments, the fluorophore absorbs at or near 488 nm to 514 nm (particularly suitable for excitation by the output of the argon-ion laser excitation source) or near 546 nm (particularly suitable for excitation by a mercury arc lamp). In other embodiment a fluorophore can emit in the NIR (near infrared region) for tissue or whole organism applications. Other desirable properties of the fluorescent label may include cell permeability and low toxicity, for example if labeling of the antibody is to be performed in a cell or an organism (e.g., a living animal).

In certain embodiments, an enzyme is a label and is conjugated to an antibody described herein. Enzymes are desirable labels because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. The enzyme substrate is selected to yield the preferred measurable product, e.g. colorimetric, fluorescent or chemiluminescence. Such substrates are extensively used in the art and are well known by one skilled in the art.

In one embodiment, colorimetric or fluorogenic substrate and enzyme combination uses oxidoreductases such as horseradish peroxidase and a substrate such as 3,3'-diaminobenzidine (DAB) and 3-amino-9-ethylcarbazole (AEC), which yield a distinguishing color (brown and red, respectively). Other colorimetric oxidoreductase substrates that yield detectable products include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants and reduced dihydroxanthenes, including dihydrofluoresceins and dihydrorhodamines including dihydrorhodamine 123. Peroxidase substrates that are tyramides represent a unique class of peroxidase substrates in that they can be intrinsically detectable before action of the enzyme but are "fixed in place" by the action of a peroxidase in the process described as tyramide signal amplification (TSA). These substrates are extensively utilized to label antigen in samples that are cells, tissues or arrays for their subsequent detection by microscopy, flow cytometry, optical scanning and fluorometry.

In another embodiment, a colorimetric (and in some cases fluorogenic) substrate and enzyme combination uses a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or O-nitrophenyl phosphate or with a fluorogenic substrate such as 4-methylumbelliferyl phosphate, 6,8-difluoro-7-hydroxy-4-methylcoumarinyl phosphate fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates.

Glycosidases, in particular beta-galactosidase, beta-glucuronidase and beta-glucosidase, are additional suitable enzymes. Appropriate colorimetric substrates include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranoside. In one embodiment, fluorogenic substrates include resorufin beta-D-galactopyranoside, fluorescein digalactoside (FDG), fluorescein diglucuronide and their structural variants, 4-methylumbelliferyl beta-D-galactopyranoside, carboxyumbelliferyl beta-D-galactopyranoside and fluorinated coumarin beta-D-galactopyranosides.

Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

In another embodiment, haptens such as biotin, can be used as labels. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, nucleotides and the like.

In certain embodiments, fluorescent proteins may be conjugated to the antibodies as a label. Examples of fluorescent proteins include green fluorescent protein (GFP) and the phycobiliproteins and the derivatives thereof. The fluorescent proteins, especially phycobiliprotein, are particularly useful for creating tandem dye labeled labeling reagents. These tandem dyes include a fluorescent protein and a fluorophore for the purposes of obtaining a larger stokes shift wherein the emission spectra is farther shifted from the wavelength of the fluorescent protein's absorption spectra. This is particularly advantageous for detecting a low quantity of antigen in a sample wherein the emitted fluorescent light is maximally optimized, in other words little to none of the emitted light is reabsorbed by the fluorescent protein. For this to work, the fluorescent protein and fluorophore function as an energy transfer pair wherein the fluorescent protein emits at the wavelength that the fluorophore absorbs at and the fluorophore then emits at a wavelength farther from the fluorescent proteins than could have been obtained with only the fluorescent protein. Alternatively, the fluorophore functions as the energy donor and the fluorescent protein is the energy acceptor.

Medical Treatments and Uses

The anti-influenza A antibodies and binding fragments and variants thereof described herein may be used for the treatment, reduction, prevention and/or for the detection, diagnosis and/or prognosis of influenza A virus infection.

Methods of diagnosis may include contacting an antibody or an antibody fragment with a sample. Such samples may be tissue samples taken from, for example, nasal passages, sinus cavities, salivary glands, lung, liver, pancreas, kidney, ear, eye, placenta, alimentary tract, heart, ovaries, pituitary, adrenals, thyroid, brain or skin. The methods of detection, diagnosis, and/or prognosis may also include the detection of an antigen/antibody complex.

In one embodiment, the invention provides a method of treating a subject by administering to the subject an effective amount of an antibody or antigen binding fragment thereof, or a pharmaceutical composition that includes the antibody or antigen binding fragment thereof. In one embodiment, the method reduces influenza A virus infection in the subject. In another embodiment, the method prevents, reduces the risk or delays influenza A virus infection in the subject. In one embodiment, the subject is a mammal. In a more particular embodiment, the subject is human. In one embodiment, the subject includes, but is not limited to, one who is particularly at risk of or susceptible to influenza A virus infection, including, for example, an immunocompromised subject.

In one embodiment, the antibody or antigen binding fragment thereof is substantially purified (i.e., substantially free from substances that limit its effect or produce undesired side-effects). In one embodiment, the antibody or antigen binding fragment thereof is administered post-exposure, or after the subject has been exposed to influenza A virus or is infected with influenza A virus. In another embodiment, the antibody or antigen binding fragment thereof is administered pre-exposure, or to a subject that has not yet been exposed to influenza A virus or is not yet infected with influenza A virus. In one embodiment, the antibody or antigen binding fragment thereof is administered to a subject that is sero-negative for one or more influenza A subtypes. In another embodiment, the antibody or antigen binding fragment thereof is administered to a subject that is sero-positive for one or more influenza A subtypes. In another embodiment, the serostatus of the patient is unknown. In one embodiment, the antibody or antigen binding fragment thereof is administered to a subject within 1, 2, 3, 4, 5, 6 or 7 days of exposure, infection or symptom onset. In another embodiment, the antibody or antigen binding fragment thereof can be administered to a subject after 1, 2, 3, 4, 5, 6, 7, 10, 15, 20, 25, 30 or any number of days there between after exposure, infection or symptom onset.

Treatment can be a single dose schedule or a multiple dose schedule and the antibody or antigen binding fragment thereof can be used in passive immunization.

In one embodiment, the antibody or antigen binding fragment thereof is administered to a subject without administration of another antiviral medication. In another embodiment, the antibody or antigen binding fragment thereof is administered to a subject in combination with one or more antiviral medications. In one embodiment, the antibody or antigen binding fragment thereof is administered to a subject in combination with one or more small molecule antiviral medications. Small molecule antiviral medications include neuraminidase inhibitors such as oseltamivir (TAMIFLU®), zanamivir (RELENZA®) and adamantanes such as Amantadine and rimantadine.

In another embodiment, the invention provides a composition for use as a medicament for the prevention or treatment of influenza A virus infection. In one embodiment, the composition includes an antibody or antigen binding fragment thereof as described herein. In one embodiment, the composition includes an antibody or antigen binding fragment thereof as described herein as the sole antiviral medication. In another embodiment, the composition includes an antibody or antigen binding fragment thereof as described herein in combination with one or more additional antiviral medications.

The invention also provides a method of preparing a pharmaceutical composition, which includes the step of admixing a monoclonal antibody with one or more pharmaceutically-acceptable carriers, wherein the antibody is a monoclonal antibody.

The present invention also provides pharmaceutical compositions. Such compositions include a therapeutically effective amount of an antibody or antigen binding fragment thereof, and a pharmaceutically acceptable carrier. The term "pharmaceutically acceptable" as used herein, means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. In one embodiment, the pharmaceutical composition contains a therapeutically effective amount of the antibody or antigen binding fragment thereof, for example, in purified form, together with a suitable amount of carrier so as to provide the form for proper administration to the patient. The formulation should suit the mode of administration.

Dosing and Administration

As used herein, the term "dose" refers to a specific quantity of an antibody therapeutic that is taken at a specified time or at specified intervals. The term "dosing", as used herein, refers to the administration of a composition, for example, a pharmaceutical composition that includes an antibody or an antibody fragment described herein, to achieve a therapeutic objective.

A "dosing schedule" refers to both the dose and the time interval at which the dose is administered. In one embodiment, the dosing schedule is part of a treatment cycle. The term "treatment cycle", as used herein, refers to the period in which the antibody is administered followed by a period with no administration of the antibody, wherein the beginning of the subsequent cycle is marked by re-initiation of administration of the antibody such that the treatment cycle allows for a period of rest between days of administration of antibody. A treatment cycle may vary in number of days, for example, 15, 16, 17, 18, 19, 20, 21, 22, 23, 24, 25, 26, 27, 28, 29, or 30 days.

In one embodiment, the antibody is administered on more than one day. For example, the antibody may be administered once per day for one day, or once per day on two or more consecutive days, for example, the antibody may be administered once per day for 1, 2, 3, 4, 5, 6, 7, 8, 9, or 10 days. In one embodiment, the same dose of the antibody is administered on each day. In another embodiment, a different dose of the antibody is administered on one or more days. For example, a patient may receive a higher dose of antibody on a day of administration, relative to the dose received on a previous day. Alternately, a patient may receive a lower dose of antibody on one day of administration, relative to the dose received on a previous day. In another embodiment, administration of the antibody may occur over one or more treatment cycles. In one embodiment, the same dosing schedule may be repeated in a subsequent treatment cycle, i.e., after a first treatment cycle is completed In one embodiment, at least about 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1,000 mg, 1,250 mg, 1,500 mg, 1,750 mg, 2,000 mg, 2,250 mg, 2,500 mg, 2,750 mg, 3,000 mg, 3,250 mg, or 3,500 mg of anti-influenza A antibody or antigen binding fragment thereof is administered to a patient.

In one embodiment, up to 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1,000 mg, 1,250 mg, 1,500 mg, 1,750 mg, 2,000 mg, 2,250 mg, 2,500 mg, 2,750 mg, 3,000 mg, 3,250 mg or 3,500 mg of anti-influenza A antibody or antigen binding fragment thereof is administered to a patient.

In another embodiment, about 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1,000 mg, 1,250 mg, 1,500 mg, 1,750 mg, 2,000 mg, 2,250 mg, 2,500 mg, 2,750 mg, 3,000 mg, 3,250 mg or 3,500 mg of anti-influenza A antibody or antigen binding fragment thereof is administered to a patient.

In another embodiment, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1,000 mg, 1,250 mg, 1,500 mg, 1,750 mg, 2,000 mg, 2,250 mg, 2,500 mg, 2,750 mg, 3,000 mg, 3,250 mg or 3,500 mg of anti-influenza A antibody or antigen binding fragment thereof is administered to a patient.

In one embodiment, the dose provided herein is for administration to an adult of average body weight and other relevant biological characteristics. In another embodiment, the dose is for administration to an adult not of average body weight or other relevant biological characteristics (including, for example, an obese or pediatric patient), with the dose adjusted to compensate for such things as body weight or other relevant biological characteristics. In another embodiment, the dose provided herein is for administration to an infant or child, with the dose adjusted to compensate for such things as body weight and other relevant biological characteristics.

The antibodies may be administered by any convenient route, and may be administered together with other biologically active agents, for example, in combination with one or more antiviral medications such as oseltamivir (TAMIFLU®), zanamivir (RELENZA®) and adamantanes such as amantadine and rimantadine.

Administration can be systemic or local and can be administered as a single dose or in multiple doses.

Various delivery systems are known and can be used to administer anti-influenza A antibody. Methods of administration include, but are not limited to, parenteral administration, including intradermal, intramuscular, intraperitoneal, intravenous and subcutaneous administration; epidural, and mucosal routes, including, for example, intranasal, inhaled and oral routes. In a more particular embodiment, the antibody is administered parenterally, for example, intramuscularly, intravenously or subcutaneously.

In one embodiment, the antibody is administered intravenously. In a more particular embodiment, the antibody is administered using an intravenous (IV) infusion pump. In one embodiment, the antibody is administered intravenously at an infusion rate of at least about 1 mg/min, 5 mg/min, 10 mg/min, 15 mg/min or 20 mg/min, 25 mg/min, 30 mg/min, 35 mg/min, 40 mg/min, 45 mg/min or 50 mg/min. In another embodiment, the infusion rate is about 10 mg/min, 15 mg/min or 20 mg/min, 25 mg/min, 30 mg/min, 40 mg/min, or 50 mg/min. In one embodiment, the antibody is administered by IV infusion over a period time, for example, over a period of at least about 1 hour, 2 hours, 3 hours, 4 hours, 5 hours or 6 hours, and up to about 3 hours, 4 hours, 5 hours or 6 hours. In another embodiment, the antibody is administered by IV infusion over a period of time, for example, about 1 hour, 2 hours, 3 hours, 4 hours, 5 hours or 6 hours.

Kits and Articles of Manufacture

In another embodiment, an article of manufacture containing materials useful for the treatment and/or prevention of influenza A virus infection is provided. In one embodiment, the article of manufacture includes a container and a label or package insert on or associated with the container. Suitable containers include, for example, bottles, vials, and syringes and may be formed from a variety of materials, including, for example, glass or plastic. In one embodiment, the container holds a composition that is effective for treating and/or preventing influenza A virus infection. In one embodiment, the composition includes anti-influenza A antibody or a fragment thereof as described herein.

In one embodiment, the article of manufacture includes a label or package insert that indicates that the composition is used for treating and/or preventing influenza A virus infection. In one embodiment, the label or package insert indicates that the antibody or antigen binding fragment can be administered post-exposure, or after the subject has been exposed to influenza A virus or is infected with influenza A virus. In another embodiment, the label or package insert indicates that the antibody or antigen binding fragment thereof can be administered pre-exposure, or to a subject that has not yet been exposed to influenza A virus or is not yet infected with influenza A virus. In one embodiment, the label or package insert indicates that the antibody or antigen binding fragment thereof can be administered to a subject that is sero-negative for one or more influenza A subtypes. In another embodiment, the label or package insert indicates that the antibody or antigen binding fragment thereof can be administered to a subject that is sero-positive for one or more influenza A subtypes. In another embodiment, the composition is administered to a patient whose sera-status is unknown. In one embodiment, the label or package insert indicates that the antibody or antigen binding fragment thereof can be administered to a subject within 1, 2, 3, 4, 5, 6 or 7 days of exposure, infection or symptom onset. In another embodiment, the antibody or antigen binding fragment thereof can be administered to a subject after 1, 2, 3, 4, 5, 6, 7, 10, 15, 20, 25, 30 or any number of days there between after exposure, infection or symptom onset.

In one embodiment, the article of manufacture includes one or more small molecule antiviral medications in addition to an anti-influenza A antibody or fragment, including, but not limited to, neuraminidase inhibitors such as oseltamivir (TAMIFLU®), zanamivir (RELENZA®) and adamantanes such as amantadine and rimantadine.

Antibodies and fragments thereof as described in the present nvention may also be included in a kit for the diagnosis of influenza A virus infection or in a kit for monitoring vaccine immunogenicity.

EXAMPLES

Example 1

Safety and pharmacokinetics of MEDI8852 was evaluated in a double-blind, single-dose, placebo-controlled, dose-escalation study in healthy adults.

A. Subjects 40 subjects were evaluated using the following inclusion criteria: healthy male or female, aged 18 to 65 years old, weight between 45 kg and 110 kg, systolic blood pressure (BP) of less than 140 mm Hg and diastolic blood pressure of less than 90 mmHg.

B. Dose

The 40 subjects were randomized by cohort to receive a single IV dose of either MEDI8852 or placebo on Day 1 (the first day of dosing) across 4 fixed-dose cohorts. MEDI8852 was supplied as a sterile liquid drug product at a concentration of 50 mg/mL and was stored at 2° C. to 8° C. (36° F. to 46° F.). Prior to administration, MEDI8852 was diluted in 0.9% (w/v) saline in an IV bag and administered as an IV infusion. The placebo/diluent was 0.9% (w/v) saline for injection. The IV infusion was administered using an IV infusion pump through a low protein binding 0.2 μm or 0.22 μm filter with a constant infusion rate of 20 mg/min.

The 40 subjects were randomized in the following 4 cohorts:

Cohort 1: 250 mg MEDI8852 (n=6) or placebo (n=2) as a single IV infusion

Cohort 2: 750 mg MEDI8852 (n=10) or placebo (n=2) as a single IV infusion

Cohort 3: 1,500 mg MEDI8852 (n=10) or placebo (n=2) as a single IV infusion

Cohort 4: 3,000 mg MEDI8852 (n=6) or placebo (n=2) as a single IV infusion

C. Pharmacokinetics

Blood samples were collected to evaluate the pharmacokinetics (PK) of MEDI8852 using validated sandwich enzyme-linked immunosorbent assay methodology. Blood samples were taken at pre-specified time points.

The mean±standard deviation plot shown in FIG. 1 shows that MEDI8852 concentration profiles generally demonstrate an initial rapid decline followed by a slower decline.

A non-compartmental analysis (NCA) using Phenix WnNonlin (Pharsight Corporation, St. Louis, Mo.) was conducted to estimate the following PK parameters: maximum serum concentration ($C_{max}$), time to maximum serum concentration ($T_{max}$), half-life ($t_{1/2}$), area under the concentration-time curve from time 0 to t ($AUC_{0-t}$), area under the concentration-time curve from time 0 to infinity ($AUC_{0-inf}$), volume at steady state ($V_{ss}$), volume of distribution ($V_z$), and clearance (CL). The results shown in Table 1 indicate that the half-life following a single IV dose was approximately 19.4 to 22.6 days. In addition, consistent PK values for half-life, clearance (CL), and volume of distribution at steady state (Vss) among dose groups indicate that MEDI8852 PK is dose-linear.

TABLE 1

| Dose (mg) | Parameter | $t_{1/2}$ (Day) | $C_{max}$ (μg/mL) | $AUC_{last}$ (μg*Day/mL) | $AUC_{\infty}$ (μg*Day/mL) | $T_{max}$* (Day) | CL (mL/Day) | $V_{ss}$ (mL) |
|---|---|---|---|---|---|---|---|---|
| 250 | N | 6 | 6 | 6 | 6 | 6 | 6 | 6 |
|  | Mean (SD) | 22.6 (4.0) | 85.2 (16.6) | 95.3 (150) | 1000 (167) | 0.04 | 257 (52) | 7690 (1670) |
| 750 | N | 10 | 10 | 10 | 10 | 10 | 10 | 10 |
|  | Mean (SD) | 19.4 (4.6) | 235 (56.7) | 2850 (762) | 2990 (794) | 0 | 269 (79.7) | 6510 (986) |
| 1,500 | N | 10 | 10 | 10 | 10 | 10 | 10 | 10 |
|  | Mean (SD) | 20.9 (4.4) | 497 (171) | 5860 (2640) | 6360 (2570) | 0.04 | 318 (277) | 8150 (6380) |
| 3,000 | N | 6 | 6 | 6 | 6 | 6 | 6 | 6 |
|  | Mean (SD) | 21.7 (6.6) | 1110 (307) | 16600 (5520) | 17700 (6110) | 0 | 200 (111) | 5260 (741) |

$C_{max}$ = maximal observed concentration; $AUC_{\infty}$ = area under the concentration-time curve from time zero to infinity; $AUC_{\infty}$ = area under the curve from time zero to infinity; $t_{1/2}$ = terminal elimination half-life; CL = systemic clearance; $V_{ss}$ = steady slate volume of distribution after administration; N = number; SD = standard deviation.
*Median values for Tmax are reported.

D. Population Modeling and Simulation

Figure 2:
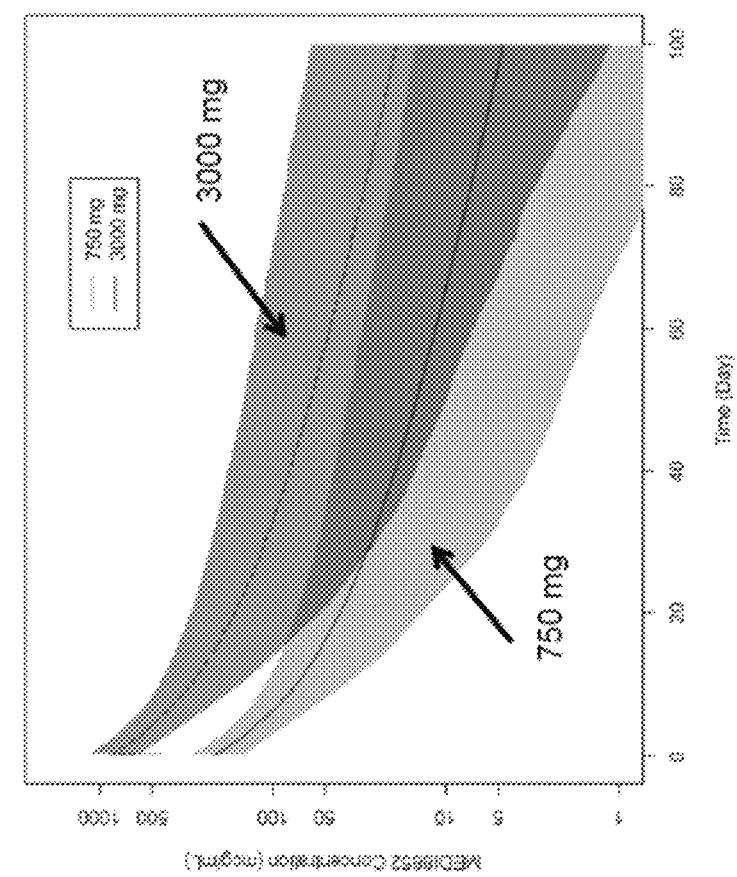
FIG. 2 is a graph showing simulated concentrations for population (n=1000 subject/group) of subjects treated with 750 mg or 3000 mg MEDI8852. The bands represent 90% confidence intervals. Solid and dotted lines represent median values for 750 and 3000 mg groups, respectively.

Population analysis was performed using NONMEM (version 7.2) (commercially available from ICON Development Solutions, Dublin, Ireland). A two-compartment model with first order elimination was used to describe the data. The NONMEM population model was then used to simulate MEDI8852 population PK (FIG. 2). The results show a good concentration separation between the 750 mg and 3,000 mg groups.

E. Anti-drug Antibodies

Blood samples were collected at Days 15(±1), 29(±2) and 101(±5) to evaluate anti-drug antibody (ADA) responses to MEDI8852 in serum using an electrochemiluminescent, solution-phase, bridging immunoassay. All ADA results were negative (i.e., no anti-drug antibody was found).

Example 2

A Phase 1b/2a clinical study using MEDI8852 is performed as follows. Outpatient individuals having influenza A virus infection are administered MEDI8852 by IV administration at a dose of 750 mg or 3000 mg. Some individuals are also administered Oseltamivir, which is the current standard of care, prior to, at the time of, or subsequent to administration of MEDI8852. Infection can be confirmed with positive rapid antigen test, or confirmed with culture, PCR or antigen testing at the study site. Treatment regimens are shown in Table 2, below.

TABLE 2

Treatment Regimen

| Cohort | Number of Subjects | Treatment Regimen |
|---|---|---|
| 1 | 40 | 75 mg oseltamivir PO BID for 5 days and 750 mg MEDI8852 as a single IV infusion |
| 2 | 40 | 75 mg oseltamivir PO BID for 5 days and 3,000 mg MEDI8852 as a single IV infusion |
| 3 | 40 | 75 mg oseltamivir PO BID for 5 days and placebo as a single IV infusion |
| 4 | 40 | 3,000 mg MEDI8852 as a single IV infusion |

Generally, a one-time dosing regimen of the antibody is contemplated, although subsequent doses may be administered.

Efficacy of MEDI8852 can be assessed using a 4-point scale (0, absent; 1, mild; 2, moderate; 3, severe) for 7 influenza symptoms (cough, nasal obstruction, sore throat, fatigue, headache, myalgia, and feverishness) twice a day through Day 10; and using an 11-point visual analog scale (0, unable to perform normal activity; 10, fully able to perform normal activity) each day through Day 10.

Duration and severity of influenza symptoms as well as time to return to ability to perform usual activities can be summarized using descriptive statistics. Time to resolution of influenza symptoms can be summarized by Kaplan-Meier curves.

The safety profile of MEDI8852+oseltamivir is similar to that of oseltamivir alone and the time to resolution of MEDI8852+oseltamivir is quicker than oseltamivir alone.

Example 3

A Phase 2b clinical study using MEDI8852 is performed as follows. Hospitalized individuals having an influenza A virus infection are administered MEDI8852 intravenously, at a dose of 250 mg, 750 mg, 1500 mg, or 3000 mg. Infection can be confirmed with positive rapid antigen test, or confirmed with culture, PCR or antigen testing at the study site. Some individuals may also be administered oseltamivir, which is the current standard of care, prior to, at the time of, or subsequent to administration of MEDI8852. Administration regimens should follow local prescribing information and can include 75 mg oseltamivir orally (PO) twice a day (BID) for 5 days. Some subjects may receive oseltamivir at doses of up to 150 mg PO BID for up to 10 days and other subjects may also receive inhaled zanamivir. Generally, a one-time dosing regimen of the antibody is contemplated, although subsequent doses may be administered.

The safety profile is similar to oseltamivir and the efficacy is better than oseltamivir alone. Efficacy can be assessed by time to normalization of respiratory function (primary endpoint), and by other secondary endpoints.

INCORPORATION BY REFERENCE

All references cited herein, including patents, patent applications, papers, text books and the like, and the references cited therein, to the extent that they are not already, are hereby incorporated herein by reference in their entirety.

SEQUENCE INFORMATION

SEQ ID NO: 1 (VH nucleotide sequence)
caggtccagctgcagcagagcggccccggactggtcaagccttcacagac
actgagcctgacatgcgccattagcggagatagcgtgagctcctacaatg
ccgtgtggaactggatcaggcagtctccaagtcgaggactggagtggctg
ggacgaacatactatagatccgggtggtacaatgactatgctgaatcagt
gaaaagccgaattactatcaacccgatacctccaagaatcagttctctc
tgcagctgaacagtgtgaccctgaggacacagccgtgtactactgcgcc

| SEQUENCE INFORMATION |
| --- |
| agaagcggccatatcaccgtctttggcgtcaatgtggatgatttcgatat<br>gtgggggcaggggactatggtcaccgtgtcaagc<br><br>SEQ ID NO: 2 (VH amino acid sequence)<br>QVQLQQSGPGLVKPSQTLSLTCAISGDSVSSYNAVWNWIRQSPSRGLEWL<br>GRTYYRSGWYNDYAESVKSRITINPDTSKNQFSLQLNSVTPEDTAVYYCA<br>RSGHITVFGVNVDAFDMWGQGTMVTVSS<br><br>SEQ ID NO: 3 HCDR1 SYNAVWN<br><br>SEQ ID NO: 4 HCDR2 RTYYRSGWYNDYAESVKS<br><br>SEQ ID NO: 5 HCDR3 SGHITVFGVNVDAFDM<br><br>SEQ ID NO: 6 (VL nucleotide sequence)<br>gatattcagatgacccagagcccttccagcctgtccgcttcagtgggga<br>tcgagtgaccattacctgccgaaccagccagagcctgagctcctacacgc |

| SEQUENCE INFORMATION |
| --- |
| actggtatcagcagaagcccggcaaagcccctaagctgctgatctacgcc<br>gcttctagtcgggggtccggagtgccaagccggttctccggatctgggag<br>tggaaccgactttaccctgacaatttcaagcctgcagcccgaggatttcg<br>ctacatactactgtcagcagagcagaactttcgggcagggcactaaggtg<br>gagatcaaa<br><br>SEQ ID NO: 7 (VL amino acid sequence)<br>DIQMTQSPSSLSASVGDRVTITCRTSQSLSSYTHWYQQKPGKAPKLLIYA<br>ASSRGSGVPSRFSGSGSGTDFTLTISSLQPEDFATYYCQQSRTFGQGTKV<br>EIK<br><br>SEQ ID NO: 8 LCDR1 RTSQSLSSYTH<br><br>SEQ ID NO: 9 LCDR2 AASSRGS<br><br>SEQ ID NO: 10 LCDR3 QQSRT |

The invention claimed is:

1. A method of inhibiting, reducing, and/or treating influenza A virus infection in a patient, the method comprising administering to the patient about 3000 mg anti-influenza A antibody or fragment thereof that is capable of binding to influenza A virus hemagglutinin and neutralizing at least one group 1 subtype and at least one group 2 subtype of influenza A virus, wherein the anti-influenza A antibody or fragment thereof comprises a HCDR1 of SEQ ID NO:3, HCDR2 of SEQ ID NO:4, and HCDR3 of SEQ ID NO:5 and a LCDR1 of SEQ ID NO:8, LCDR2 of SEQ ID NO:9 and LCDR3 of SEQ ID NO:10.

2. The method according to claim 1, wherein the administering is selected from parenteral or intravenous administration.

3. The method according to claim 2, wherein the anti-influenza A antibody or fragment thereof is administered as a single dose.

4. The method according to claim 1, wherein the anti-influenza A antibody or fragment thereof is administered before or after the patient is exposed to influenza A virus, infected with influenza A virus, exhibits symptoms of influenza A virus infection, or a combination thereof.

5. The method according to claim 4, wherein the anti-influenza A antibody or fragment thereof is administered to a subject within 30 days of exposure, infection, symptom onset, or a combination thereof.

6. The method according to claim 1, wherein the anti-influenza A antibody or fragment thereof is capable of neutralizing one or more influenza A virus group 1 subtype selected from: H1, H2, H5, H6, H8, H9, H11, H12, H13, H16, H17, H18, and variants thereof; and one or more influenza A virus group 2 subtypes selected from: H3, H4, H7, H10, H14 and H15 and variants thereof.

7. The method according to claim 1, wherein the anti-influenza A antibody or fragment thereof comprises a VH having an amino acid sequence with at least 75% identity to the amino acid sequence of SEQ ID NO: 2 and a VL having an amino acid sequence with at least 75% identity to the amino acid sequence of SEQ ID NO:7.

8. The method according to claim 1, wherein the anti-influenza A antibody or fragment thereof comprises a VH having an amino acid sequence shown in SEQ ID NO: 2 and a VL having an amino acid sequence shown in SEQ ID NO: 7.

9. The method according to claim 1, wherein the anti-influenza A antibody comprises MEDI8852.

10. The method according to claim 1, wherein the antibody or fragment thereof is administered in combination with one or more small molecule antiviral medications.

11. The method according to claim 10, wherein the small molecule antiviral medication is selected from oseltamivir, zanamivir, amantadine and rimantadine.

* * * * *

SEQUENCE LISTING

<160> NUMBER OF SEQ ID NOS: 10

<210> SEQ ID NO 1
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtccagc tgcagcagag cggccccgga ctggtcaagc cttcacagac actgagcctg      60
acatgcgcca ttagcggaga tagcgtgagc tcctacaatg ccgtgtggaa ctggatcagg     120
cagtctccaa gtcgaggact ggagtggctg ggacgaacat actatagatc cgggtggtac     180
aatgactatg ctgaatcagt gaaaagccga attactatca accccgatac ctccaagaat     240
cagttctctc tgcagctgaa cagtgtgacc ctgaggaca cagccgtgta ctactgcgcc      300
agaagcggcc atatcaccgt ctttggcgtc aatgtggatg ctttcgatat gtgggggcag    360
gggactatgg tcaccgtgtc aagc                                           384

<210> SEQ ID NO 2
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Tyr
            20                  25                  30

Asn Ala Val Trp Asn Trp Ile Arg Gln Ser Pro Ser Arg Gly Leu Glu
        35                  40                  45

Trp Leu Gly Arg Thr Tyr Tyr Arg Ser Gly Trp Tyr Asn Asp Tyr Ala
    50                  55                  60

Glu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Gly His Ile Thr Val Phe Gly Val Asn Val
              100                 105                 110

Asp Ala Phe Asp Met Trp Gly Gln Gly Thr Met Val Thr Val Ser Ser
        115                 120                 125

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Tyr Asn Ala Val Trp Asn
1               5

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Thr Tyr Tyr Arg Ser Gly Trp Tyr Asn Asp Tyr Ala Glu Ser Val
1               5                   10                  15

Lys Ser

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Gly His Ile Thr Val Phe Gly Val Asn Val Asp Ala Phe Asp Met
1               5                   10                  15

<210> SEQ ID NO 6
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gatattcaga tgacccagag cccttccagc ctgtccgctt cagtggggga tcgagtgacc      60
attacctgcc gaaccagcca gagcctgagc tcctacacgc actggtatca gcagaagccc     120
ggcaaagccc ctaagctgct gatctacgcc gcttctagtc gggggtccgg agtgccaagc     180
cggttctccg gatctgggag tggaaccgac tttaccctga caatttcaag cctgcagccc     240
gaggatttcg ctacatacta ctgtcagcag agcagaactt cgggcaggg cactaaggtg     300 gagatcaaa                                                            309

<210> SEQ ID NO 7
<211> LENGTH: 103
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Tyr
            20                  25                  30

Thr His Trp Tyr Gln Gln Lys Pro Gly Lys Ala Pro Lys Leu Leu Ile
        35                  40                  45

Tyr Ala Ala Ser Ser Arg Gly Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
                85                  90                  95

Gly Thr Lys Val Glu Ile Lys
            100

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Thr Ser Gln Ser Leu Ser Ser Tyr Thr His
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Ser Ser Arg Gly Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Ser Arg Thr
1               5
```